United States Patent
Pham

(10) Patent No.: US 12,251,530 B2
(45) Date of Patent: Mar. 18, 2025

(54) SYNCHRONIZED AUTOMATED BRONCHIAL LAVAGE ASPIRATION APPARATUS

(71) Applicant: Thach Pham, Apo, AE (US)

(72) Inventor: Thach Pham, Apo, AE (US)

(73) Assignee: PHAM & RODRIQUEZ INNOVATIONS LLC, Edmonds, WA (US)

( * ) Notice: Subject to any disclaimer, the term of this patent is extended or adjusted under 35 U.S.C. 154(b) by 811 days.

(21) Appl. No.: 17/342,103

(22) Filed: Jun. 8, 2021

(65) Prior Publication Data

US 2021/0379275 A1 Dec. 9, 2021

Related U.S. Application Data

(60) Provisional application No. 63/036,933, filed on Jun. 9, 2020.

(51) Int. Cl.
*A61M 3/02* (2006.01)
*A61M 16/00* (2006.01)
(Continued)

(52) U.S. Cl.
CPC ...... *A61M 3/0254* (2013.01); *A61M 16/0057* (2013.01); *A61M 16/04* (2013.01); *A61M 25/007* (2013.01); *A61M 25/0108* (2013.01); *A61M 2205/3331* (2013.01); *A61M 2210/1035* (2013.01)

(58) Field of Classification Search
CPC ............ A61M 3/0254; A61M 16/0057; A61M 16/04; A61M 25/007; A61M 25/0108; A61M 2205/3331; A61M 2210/1035; A61M 1/74; A61M 1/77; A61M 3/0283; A61M 16/0833; A61M 2210/1032; A61M 16/0486; A61M 16/0051; A61M 16/024; A61M 16/0477; A61M 2016/0027; A61M 2205/502; A61M 16/0463; A61M 16/0009
See application file for complete search history.

(56) References Cited

U.S. PATENT DOCUMENTS

| | | | |
|---|---|---|---|
| 4,398,910 A | 8/1983 | Blake | |
| 9,750,910 B2 * | 9/2017 | Chaturvedi | ....... A61M 16/0463 |

(Continued)

FOREIGN PATENT DOCUMENTS

| | | |
|---|---|---|
| CN | 110975029 A | 4/2020 |
| JP | 2008073060 A | 4/2008 |
| WO | 2021021023 A1 | 2/2021 |

OTHER PUBLICATIONS

International Patent Application No. PCT/US2021/036554, International Search report mailed Nov. 5, 2021, 3 pages.

(Continued)

*Primary Examiner* — Theodore J Stigell
(74) *Attorney, Agent, or Firm* — Leber IP LAW; Celia H. Leber

(57) ABSTRACT

A synchronized automated bronchial lavage aspiration apparatus synchronizes with ventilator inspiration and expiration cycles to clear a patient's airway of stagnant secretion automatically. Synchronized and automatic instillation of saline prior to aspiration suppresses bacteria in the airway and suctioning during exhalation drains the airway of sputum.

18 Claims, 11 Drawing Sheets

(51) Int. Cl.
*A61M 16/04* (2006.01)
*A61M 25/00* (2006.01)
*A61M 25/01* (2006.01)

(56) References Cited

U.S. PATENT DOCUMENTS

2008/0023005 A1* 1/2008 Tokunaga ......... A61M 16/0484
128/205.19
2015/0190598 A1* 7/2015 Hashimoto ....... A61M 16/0463
128/204.23

OTHER PUBLICATIONS

Kolobow, et al., "The Mucus Slurper: a novel tracheal tub that requires no tracheal tube suctioning. A preliminary report", Intensive Care Med (2006) 32, published online Jul. 7, 2006, pp. 1414-1418.

Mario Solomita DO, et al., Humidification and Secretion vol. in Mechanically Ventilated Patients, Respiratory Care, Oct. 2009, 1329-1335, vol. 54, No. 10.
Pedro Caruso, MD, et al., Instillation of normal saline before suctioning reduces the incidence of pneumonia in intubated and ventilated adults, Synopsis, Australian Journal of Physiotherapy, 2009, 136, vol. 55.
F. Álvarez Lerma, et al., Guidelines for the prevention of ventilator-associated pneumonia and their implantation, Medicina Intensiva, 2014, 226-236, 38(4).
Michaerl Klompas, MD, et al., Strategies to Prevent Ventilator-Associated Pneumonia in Acute Care Hospitals: 2014 update, Infection Control and Hospital Epidemiology, Aug. 2014, pp. 915-936, vol. 35, No. 8.
Tokmaji G., et al., Silver-coated endotracheal tubes for prevention of ventilator-associated pneumonia in critically ill patients, Cochrane Database of Systematic Reviews, 2015, Issue 8, Art. No. CD009201.
Andrea Coppadoro, et al., Non-Pharmacological Interventions to Prevent Ventilator-Associated Pneumonia: A Literature Review, Respiratory Care, Dec. 2019, pp. 1586-1595, vol. 64, No. 12.

* cited by examiner

SYNCHRONIZED AUTOMATED BRONCHIAL LAVAGE ASPIRATION APPARATUS

CLAIM OF PRIORITY TO PROVISIONAL APPLICATION (35 U.S.C. & 119(e))

This application claims priority under 35 U.S.C. § 119(e) from provisional patent Application No. 63/036,933 filed on Jun. 9, 2020. The 63/036,933 application is incorporated herein by reference.

FIELD OF THE INVENTION

The present invention relates to a mechanical ventilator that moves air in and out of a patient's lungs. More specifically, the invention relates to a mechanical automated bronchial lavage aspiration system that synchronizes the ventilator's inspiration and expiration cycles in order to clear the airway of stagnant secretion in order to prevent ventilator-associated pneumonia.

BACKGROUND OF THE INVENTION

Ventilator-associated pneumonia (VAP) is the most frequent ICU-acquired infection and a significant cause of morbidity and mortality despite improvements in prevention strategies and antibiotics. VAP is associated with prolonged mechanical ventilation by 7-11 days, hospitalization by 11-13 days, and an excess cost of $40,000-$57,000 per patient. The primary route of infection is micro-aspiration of bacteria from the oropharynx and upper GI tract. Ventilator airflow moves pathogens toward the distal airways while clearance of the trachea is blunted due to reduced ciliary movement and impaired cough. Bacteria in conjunction with airway sputum leads to an ideal media for VAP. The rate of sputum production in ventilated patients has been reported in the literature to be 1-5 cc/hr. See Solomita, et al., Humidification and Secretion Volume in Mechanically Ventilated Patients, Respiratory Care 2009, 54(10) ("Solomita"), 1329-1335. In-line endotracheal lavage and suction performed by medical staffs is a standard practice in ICU worldwide. Instillation of saline prior to aspiration has been proven to reduce VAP. See Caruso, et al., Instillation of normal saline before suctioning reduces the incidence of pneumonia in intubated and ventilated adults, Synopsis, Australian Journal of Physiotherapy, 2009, 136, Vol. 55. We propose a mechanical automated bronchial lavage aspiration system which synchronizes with ventilator inspiration and expiration cycle in order to clear the airway of stagnant secretion, prevent VAP, reduce healthcare cost, and eliminate the frequent need for ICU staffs hands-on intervention. Current Guidelines and Devices to Prevent Ventilator-Associated Pneumonia Basic practices to prevent VAP include avoiding intubation when possible, minimizing transport while ventilated, implementation of weaning protocols, minimizing sedation, maintaining physical condition, minimizing pooling of secretions above endotracheal tube cuff, elevation of head of the bed, and maintaining ventilator circuits. See F. Alvarez Lerma, et al., Guidelines for the prevention of ventilator-associated pneumonia and their implantation, Medicina Intensiva 2014, 38(4), 226-236.

Several medical devices/therapeutics have been designed to address and prevent VAP with debatable effectiveness. For example, the Mallinckrodt (Medtronic) Hi-Lo EVAC (expired trademark Registration U.S. Pat. No. 2,555,293) tube is a specially designed endotracheal tube with subglottic aspiration and has been shown to reduce VAP from 21 to 13% but no significant difference in mortality, ICU stay, duration of mechanical ventilation, or antibiotic use. See Klompas, M., et al., Strategies to prevent ventilator-associated pneumonia in acute care hospitals: 2014 update, Infection Control and Hospital Epidemiology, 35:915.

Silver is known to have anti-microbial effect and silver-coated endotracheal tube (ETT) has been designed to prevent VAP. Silver-coated endotracheal tubes have been shown to decrease VAP and are associated with delayed time to VAP occurrence compared with noncoated ETT See Tokmaji et al., Silver-coated endotracheal tubes for prevention of ventilator-associated pneumonia in critically ill patients, Cochrane Database of Systematic Reviews 2015, Issue 8. Art. No.: CD009201. DOI: 10.1002/14651858.CD009201.pub2. However, silver-coated ETT has no statistically significant in terms of mortality, duration of intubation, length of hospital and ICU stay.

Endotracheal tube biofilm removal devices, such as the Ballard Restore2 by Avanos ("Ballard Restore2" is a pending U.S. trademark application, Serial No. 90/674,751 filed Apr. 27, 2021 by Avent, Inc.), and the Rescue Cath by Omneotech® ("Omneotech" is U.S. trademark Registration U.S. Pat. No. 3,999,066 and "Rescue Cath" is claimed by it as a trademark) are commercially available to assist with removal of biofilm build-up within the ETT, however, its benefits and efficacy at reducing VAP and its impact on relevant outcomes such as duration of ventilation and mortality, cost-benefit ratio, are still unclear. See Andrea Coppadoro, et al., Non-Pharmacological Interventions to Prevent Ventilator-Associated Pneumonia: A Literature Review, Respiratory Care, December 2019, 64(12), 1586-1595.

Kinetic ICU beds have also been used to place ventilated patients in strapped-in/prone position to reduce incidence of VAP, however, position patients prone has not been shown to decrease VAP.

SUMMARY OF THE INVENTION

The Synchronized Automated Bronchial Lavage Aspiration ("SABLA") apparatus of the present invention is a machine which allows synchronized, automated, and programmable irrigation/lavage and suction/aspiration of the tracheal and bronchial trees in patients on a mechanical ventilator due to respiratory failure to prevent pulmonary blockage, distress, and infection. The irrigation/lavage of saline, mucolytics, and/or other medications into the trachea and bronchi is synchronized with inhalation cycle of the mechanical ventilator. In addition, the suction/aspiration of the endotracheal tube, trachea, and bronchi is synchronized with the exhalation cycle of the mechanical ventilator. The dual action of the irrigation/lavage and suction/aspiration of the airway is accomplished via dual function catheter situated within the endotracheal tube and airway. The SABLA Control Module allows for the synchronized function with any mechanical ventilator via a pressure sensor, allows precise measurements of input and output, and allows the medical staffs to program and adjust settings based on patient clinical situations. This device will prevent pulmonary infection, shorten ventilator time, cut healthcare cost, and reduce morbidity/mortality.

The following summarizes disclosed embodiments of the present invention:

1. A synchronized automated bronchial lavage aspiration apparatus for use with an endotracheal tube, comprising:

(a) a drainage pump and a drainage conduit extending from the drainage pump, (b) a catheter having a catheter proximal end and a catheter distal end, a catheter length between the catheter proximal end and the catheter distal end, a catheter outer surface along the catheter length, and an interior channel within the catheter outer surface in fluid communication at the proximal end of the catheter with the drainage conduit, said interior channel having at least one opening proximal to the catheter distal end, wherein the catheter is sized for insertion into an endotracheal tube during ventilation, (c) a pressure sensor sensing positive pressure in the endotracheal tube associated with exhalation by a patient and negative pressure in the endotracheal tube associated with inhalation by the patient, wherein the pressure sensor generates an exhalation pressure signal responsive to the positive pressure associated with exhalation, and (d) a control processor to receive the exhalation pressure signal from the pressure sensor over a communication link from the pressure sensor, wherein the control processor synchronizes and automates suction by the drainage pump according predetermined suction parameters, including frequency, duration and interval of suction, in response to the positive pressure associated with exhalation, wherein said suction draws aspirates from the at least one opening into the interior channel of the catheter and into the drainage conduit.

2. The synchronized automated bronchial lavage aspiration apparatus of Summary 1, above, further comprising:
(a) an irrigation pump and an irrigation conduit extending from the irrigation pump,
(b) wherein the interior channel within the catheter is in fluid communication at the proximal end of the catheter with the irrigation conduit,
(c) the pressure sensor further generating an inhalation pressure signal responsive to the negative pressure associated with inhalation by the patient, and
(d) wherein the control processor further synchronizes and automates pumping irrigation solution from the irrigation pump according to predetermined irrigation parameters, including frequency, duration and interval of pumping irrigation solution, through the irrigation conduit and the interior channel and out the at least one opening of the catheter in response to receiving the inhalation pressure signal associated with inhalation.

3. The synchronized automated bronchial lavage aspiration apparatus of Summaries 1 or 2, wherein aspirates pumped by the drainage pump into the drainage conduit are received by a control module and analyzed by the control processor for clinical parameters, including aspirate volume, clarity and vicosity, and wherein the control processor adjusts the predetermined drainage parameters and the predetermined irrigation parameters according to the clinical parameters.

4. The synchronized automated bronchial lavage aspiration apparatus of Summary 3, wherein the control module further comprises a screen to display predetermined drainage parameters and predetermined irrigation parameters and clinical parameters, and wherein the control module further comprises a keypad to input directions to the control processor to adjust the predetermined drainage parameters and predetermined irrigation parameters and clinical parameters.

5. The synchronized automated bronchial lavage aspiration apparatus of Summary 4, wherein the control processor displays recommended medication to be added to the irrigation solution in response to the predetermined drainage parameters and predetermined irrigation parameters and clinical parameters analyzed by the control processor.

6. The synchronized automated bronchial lavage aspiration apparatus of Summary 1, 2, 3, 4 or 5, wherein the at least one opening through the catheter further comprises a plurality of ports through the catheter outer surface.

7. The synchronized automated bronchial lavage aspiration apparatus of Summary 1 or 2, wherein the at least one opening through the catheter is formed by a side opening groove in the catheter outer surface along the catheter length.

8. The synchronized automated bronchial lavage aspiration apparatus of Summary 1, further comprising:
(a) an irrigation pump and an irrigation conduit extending from the irrigation pump,
(b) an irrigation channel within the catheter and fluidly separated from the interior channel, wherein the irrigation channel is in fluid communication at the proximal end of the catheter with the irrigation conduit, and wherein the irrigation channel is in fluid communication with an irrigation port through the catheter outer surface proximal to the catheter distal end,
(c) the pressure sensor further generating an inhalation pressure signal responsive to the negative pressure associated with inhalation by the patient, and
(d) wherein the control processor further synchronizes and automates pumping irrigation solution from the irrigation pump according to predetermined parameters, including frequency, duration and interval of pumping irrigation solution, through the irrigation conduit and the irrigation channel and out the irrigation port in response to receiving the inhalation pressure signal associated with inhalation.

9. The synchronized automated bronchial lavage aspiration apparatus of Summary 9, wherein the interior channel of the catheter is a drainage channel and the at least one opening through the catheter is a drainage opening and wherein the drainage opening is formed by a side opening groove in the catheter outer surface along the catheter length.

10. The synchronized automated bronchial lavage aspiration apparatus of Summary 1, 2, 3, 4, 5, 6, 7, 8, 9, or 10, further comprising a radio opaque marker located at the catheter distal end.

11. The synchronized automated bronchial lavage aspiration apparatus of Summary 1, 2, 3, 4, 5, 8, 9 or 10, wherein the catheter has a longitudinal axis along the catheter length and an oval cross section having opposite vertices, and wherein the at least one drainage opening comprises a pair of drainage openings, wherein each of the pair of drainage openings is aligned with one of the opposite vertices, and wherein each of the pair of drainage openings comprises the drainage channel side opening groove along at least a portion of the catheter outer surface along each opposite vertex.

12. The synchronized automated bronchial lavage aspiration apparatus of Summary 1, 2, 3, 4, 5, 8, 9 or 10, wherein the catheter has a longitudinal axis along the catheter length and an catheter cross section, and wherein the at least one drainage opening comprises a trio of drainage openings, wherein each of the tri of drainage openings is aligned about the longitudinal axis, and wherein each of the trio of drainage openings comprises the drainage channel side opening groove along at least a portion of the catheter outer surface.

13. The synchronized automated bronchial lavage aspiration apparatus of Summary 1, 2, 3, 4, or 5, wherein the catheter distal end comprises a split-end catheter having a left catheter end adapted to extend into a left main bronchus and a right catheter end adapted to extend into a right main bronchus.

14. The synchronized automated bronchial lavage aspiration apparatus of Summary 1, 2, 3, 4, 5, 6, 7, 8, 9, 10, 11, 12 or 13, further comprising:
   (a) an external tube containing the drainage conduit and irrigation conduit and joining the catheter proximal end,
   (b) a protective sheath surrounding the external tube and catheter, wherein the external tube or catheter may be grasped within the protective sheath, and
   (c) a junction with a first connector to receive a ventilation tube from a ventilator, a second connector to receive the external tube and catheter and protective sheath, and a third connector to receive an endotracheal tube, wherein the first, second and third connectors of the junction admit to a common space, and wherein the first and second connectors are oriented to allow the external tube and catheter to pass into the endotracheal tube.

15. The synchronized automated bronchial lavage aspiration apparatus of Summary 1, 2, 3, 4, 5, 6, 7, 8, 9, 10, 11, 12, 13, 14 or 15, further comprising a junction pressure sensor in communication with the common space to sense pressure within the common space and the endotracheal tube associated with exhalation and inhalation and to generate the exhalation pressure signal and the inhalation pressure signal and transmit the exhalation pressure signal or the inhalation pressure signal through the communication link to the control processor.

16. The synchronized automated bronchial lavage aspiration apparatus of Summary 1, 2, 3, 4, 5, 6, 7, 8, 9, 10, 11, 12, 13, 14, 15, or 16, wherein the communication link to the control processor is a wire.

17. The synchronized automated bronchial lavage aspiration apparatus of Summary 1, 2, 3, 4, 5, 6, 7, 8, 9, 10, 11, 12, 13, 14, 15 or 16, wherein the communication link to the control processor is a wireless connection.

DETAILED DESCRIPTION OF THE INVENTION

Figure 1:
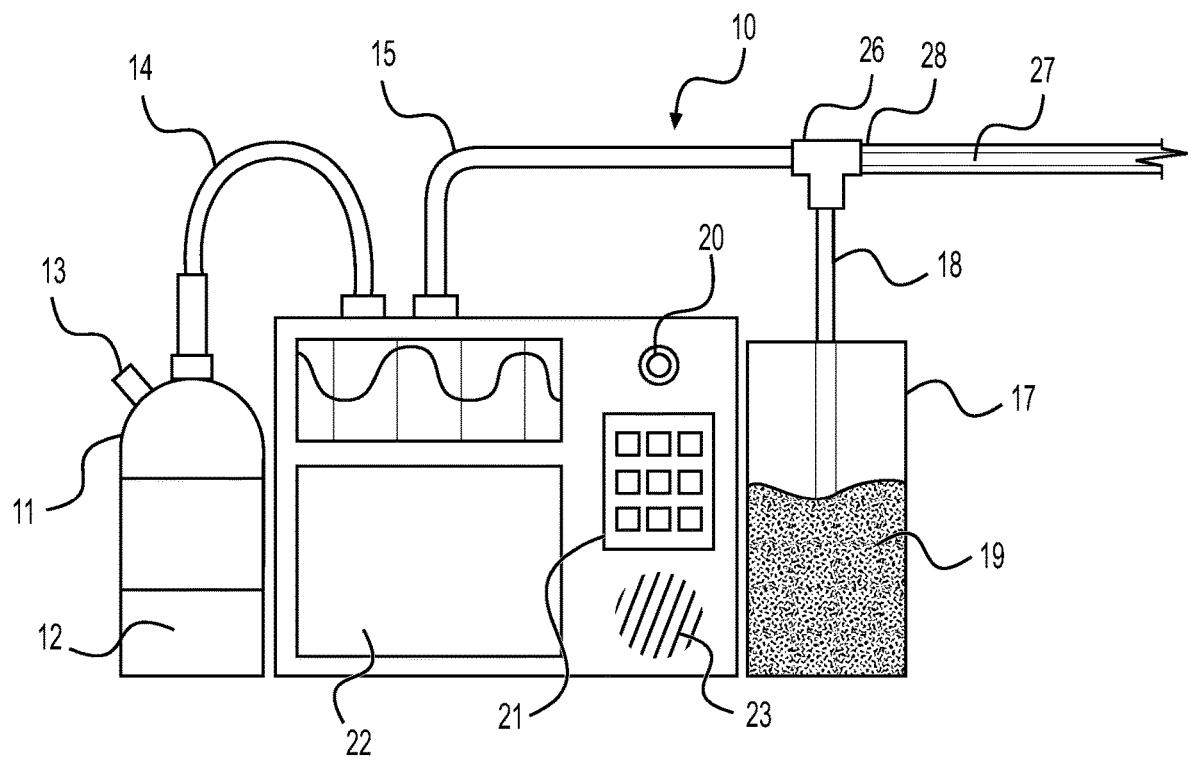
FIG. 1 is a schematic of the SABLA control module, solution and drainage containers, and catheter of the present invention.
Figure 5:
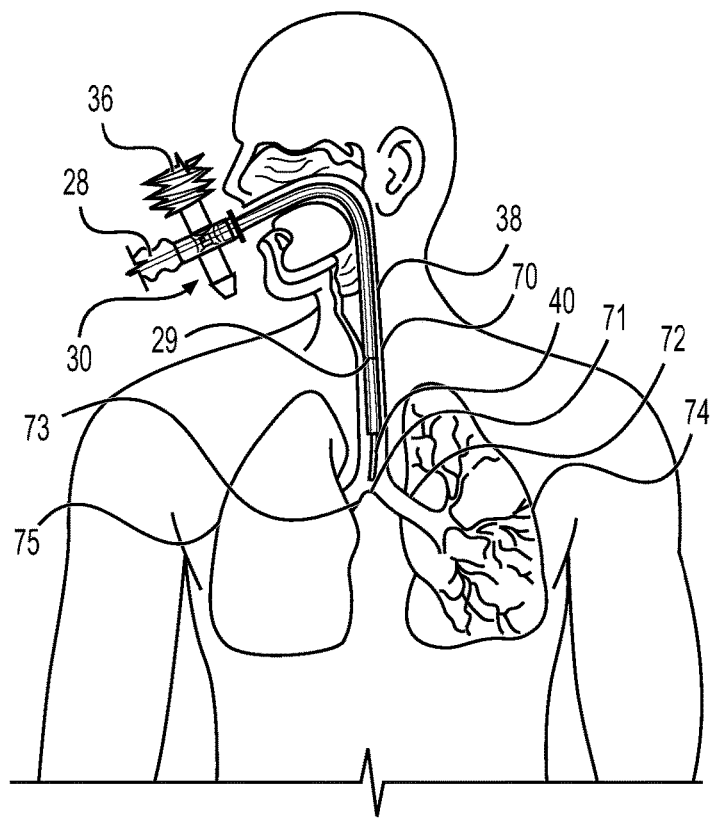
FIG. 5 is a diagram of the junction between the SABLA catheter, ventilator tubing, and endotracheal tube, as well as the catheter positioned within upper airway and extending into the trachea of a patient.

FIG. 1 shows the control module 10, which houses electronics, pumps, and mechanics for the synchronized automated bronchial lavage aspiration ("SABLA") apparatus of the present invention. The control module 10 regulates bronchial lavage/aspiration and drainage/exhalation. The control module 10 is attached to an irrigation fluid container 11 and a drainage container 17. The irrigation fluid container 11 holds the irrigation fluid 12, usually a saline solution. A medication port 13 in the irrigation fluid container 11 allows the addition of medication, antibiotics, mucolytics, etc., to the irrigation fluid 12. The irrigation fluid 12, along with any added medication, is then pumped by the control module 10 from the irrigation fluid container 11 through an irrigation supply pipe 14. A drainage container 18 receives and collects trancheo-bronchial aspirates 19 through a drainage intake 18. The control module 10 synchronizes the output of irrigation fluid 12 and the suctioning of tracheo-bronchial aspirates (78, as shown in FIGS. 3A-3C and 8A-8C, and described in more detail below). From the control module 10, the irrigation fluid 12 is pumped via a pumping conduit 15 to an external tube 27 to a catheter, such as the catheter 40 shown in FIGS. 3A through 3D. Aspirates 78 are pumped from the trachea 70 of a patient (as shown in FIG. 5) by the catheter 40 to the external tube 27, through the pumping conduit 15, to the drainage intake 18, and then into the drainage container 17. The control module 10 synchronizes the supply of irrigation fluid 12 with a ventilator's inspiration cycle in order to treat the trachea 70 and bronchi (72 and 73), and then synchronizes the suctioning of aspirates 78 with the ventilator's expiration cycle in order to clear the airway 70 of stagnant secretions 78.

Figure 10A:
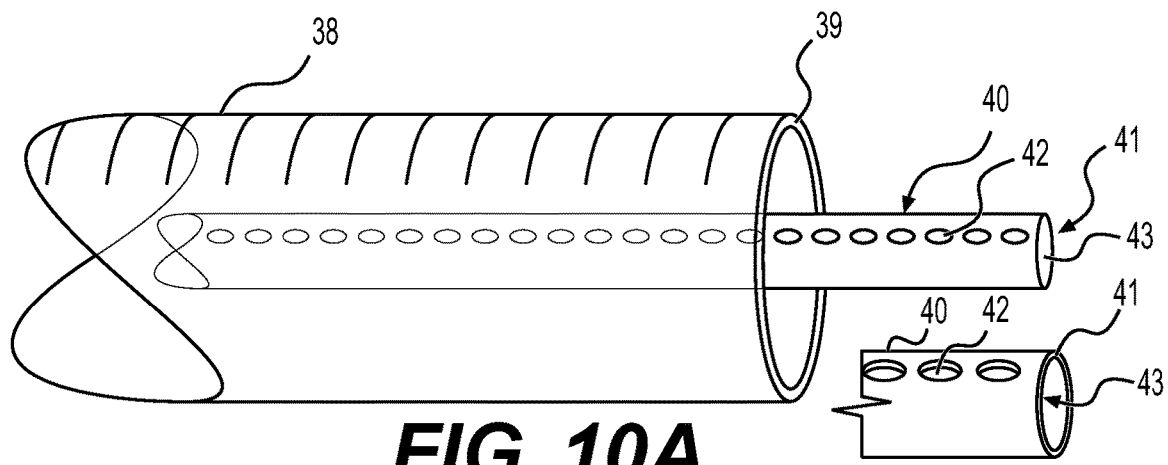
FIG. 10A shows a side view of an embodiment of the SABLA catheter within an endotracheal tube as well as an enlargement of the distal end of the catheter.

FIG. 10A shows details of one embodiment of a catheter 40 of the present invention within a ventilator's conventional endotracheal tube ("ETT") 38. On the outer surface of the catheter 40 along the catheter's 40 length are a multitude of ports 42 to spray 45 irrigation fluid 12 from the catheter 40 toward the inside of the ETT 38 and the trachea 70 (as shown in FIG. 3B). A typical ETT 38 for an adult will have a cross section of approximately ten millimeters. The catheter has a cross section of approximately two to three millimeters at its widest, which allows the ventilator to function without significant restriction. The ETT is placed in a patient's trachea 70 (as shown in FIG. 5) near the carina 71 where the left and right bronchi, 72 and 73, and the distal end 41 of the catheter 40 extends about one to two centimeters beyond the distal end 39 of the ETT 38. During the ventilator's inspiration cycle (indicated by arrow 76 in FIG. 3B), the control module 10 pumps irrigation fluid 12 through ports 42, indicated by the spray 45. Five to ten cubic centimeters (5-10 cc) saline irrigation solution 12 volume is adequate per cycle, although off course quantities and intervals can be adjusted for the particular patient and treatment needs. During the ventilator's expiration cycle, the control module 10 sucks aspirates 78 out of the trachea 70 through the catheter's open distal end 41, as well as through ports 42, and into the interior channel 43, as indicated by arrow 77 in FIG. 3C and further illustrated in FIGS. 8C and 8D. FIGS. 3D and 8E show the trachea 70 cleared of aspirates 78. Five to one hundred millimeter of mercury (5-100 mmHg) suction pressure is a wide enough range for bronchial aspiration, adjusted for the particular patient and treatment needs. During the first few inspiration/expiration cycles, secretions, plugs or fluid returns may not be observed when instilling saline solution in the trachea, but, with more cycles (when the lung is seeing 50 cc or more fluids) some fluid collection will be observed. Also, a larger fluid lavage/installation with the first cycle may be efficacious and can be followed with 5-10 cc in subsequent cycles. Additionally, nebulizing the solution will disperse the saline more evenly and improve the efficiency of the lavage.

Referring to FIGS. 3A through 3D, 5, 8A through 8E, and 9A and 9B, an ETT 38 is first positioned within a patient's trachea 70. In one embodiment, shown in FIGS. 5 and 9A, the catheter 40 is inserted into the ETT 38 until it extends about two to three millimeters beyond the end of the ETT 39, but above the carina 61 (shown in FIGS. 5 and 9A). During the inspiration cycle, indicated by arrow 76 in FIG. 3B, sputum and other aspirates 78 that have accumulated in the trachea 70 and ETT 38 will be treated with the irrigation fluid 12 and sucked out by the catheter 40 during the ventilator's expiration cycle, as indicated by arrow 77 in FIG. 3C. In a modified embodiment, shown in FIG. 9B, the catheter 40 has a split end 46 with a left bronchus end 46L, that extends into the left main bronchus 72, and a right bronchus end 46R, that extends into the left main bronchus 73. The left bronchus end 46L will supply irrigation fluid 12 into the left main bronchus 72 and the right bronchus end 46R will supply irrigation fluid into the left main bronchus 73. Aspirates 78 that have accumulated in the left lung 74 will be sucked out from the left main bronchus 72 through the left bronchus end 46L and aspirates 78 that have accumulated in the right lung 75 will be sucked out from the right main bronchus 73 through the right bronchus end 46R.

Figure 4:
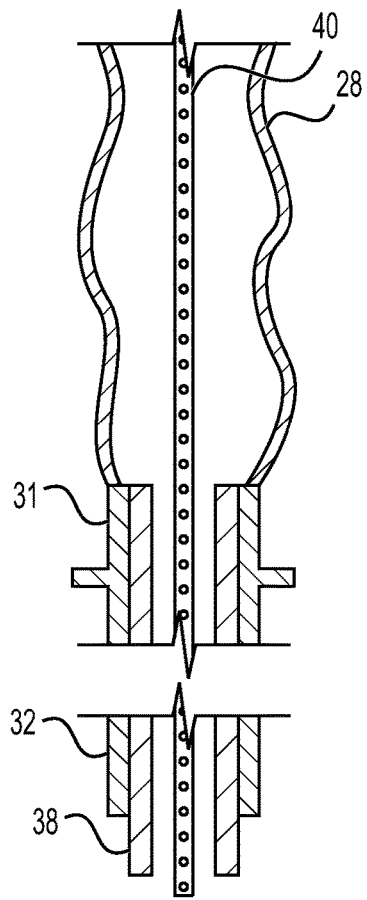
FIG. 4 shows the SABLA catheter within its protective sheath and extending into the endotracheal tube.
Figure 6:
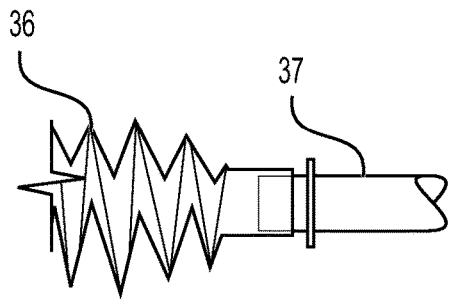
FIG. 6 shows a section of a ventilator's tubing and connector to the junction.
Figure 7:
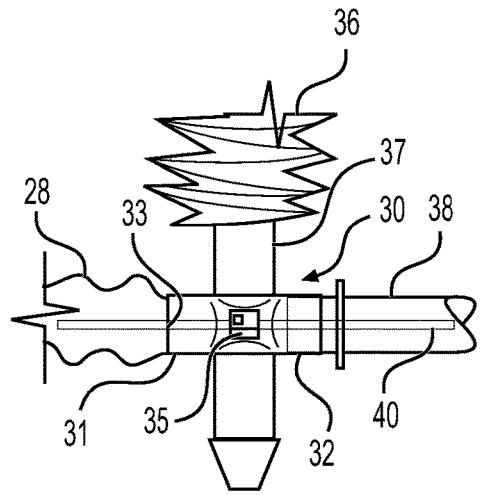
FIG. 7 is a side view of the SABLA catheter within its protective sheath, junction, ventilator tubing, pressure sensor, and catheter within the endotracheal tube.

FIGS. 4 through 8E show the arrangement of the external tube portion 27, catheter 40, ETT 38, and the three-way junction 30 between them and the ventilator tubing 36 to the ventilator (not shown). FIG. 4 shows the catheter 40 surrounded by the protective sheath 28, terminating in a connector 31. The protective sheath 28 prevents outside contaminants from reaching the catheter 40, thereby maintaining the sterility of the catheter before it is introduced into the ETT 38 and trachea 70. The protective sheath 28 is thin and flexible so that an operator may grasp the catheter 40 or external tube 27 (or 27', 27" or 27''') through the protective sheath 28 and extend or withdraw the catheter 40 into the ETT 38 and trachea 70. The connector 31 joins one branch of the junction 30. The outer surface of the catheter 40 passes through a flexible seal 33 that keeps outside air and fluids from entering the ETT 38, while allowing the catheter to be extended or withdrawn. The catheter 40 passes through the junction 30 and enters the ETT 38 through connector 32. To extend or withdraw the catheter 40 into or from the ETT 38, an operator can manually grasp the catheter 40 through the protective sheath 28 and push it forward into the ETT 38 and trachea 70 or pull it out. Referring to FIG. 7, the catheter 40, surrounded by the protective sheath 28, connects to the junction 30, such as by a tubular friction fit. A conventional ventilator's ventilation tube 36 connects to another branch 37 of the junction 30, as shown in FIG. 6. In a similar manner, shown in FIG. 7, the ETT 38 connects to yet another branch 32 of the junction 30 by a tubular friction fit. Through the junction 30 the catheter 40 passes into the ETT 38. The junction 30 forms a sealed interior space that communicates with the ETT 38. The junction 30 may include a pressure sensor 35 that will detect positive pressure during inhalation and negative pressure during exhalation. The pressure sensor 35 is connected wirelessly or by wire to the control module 10 in order to synchronize the irrigation/lavage and drainage cycles with inhalation and exhalation, respectively. Alternatively, the pressure sensor of a conventional ventilator may be used to pass information to the control module 10 for this synchronization.

Figure 2:
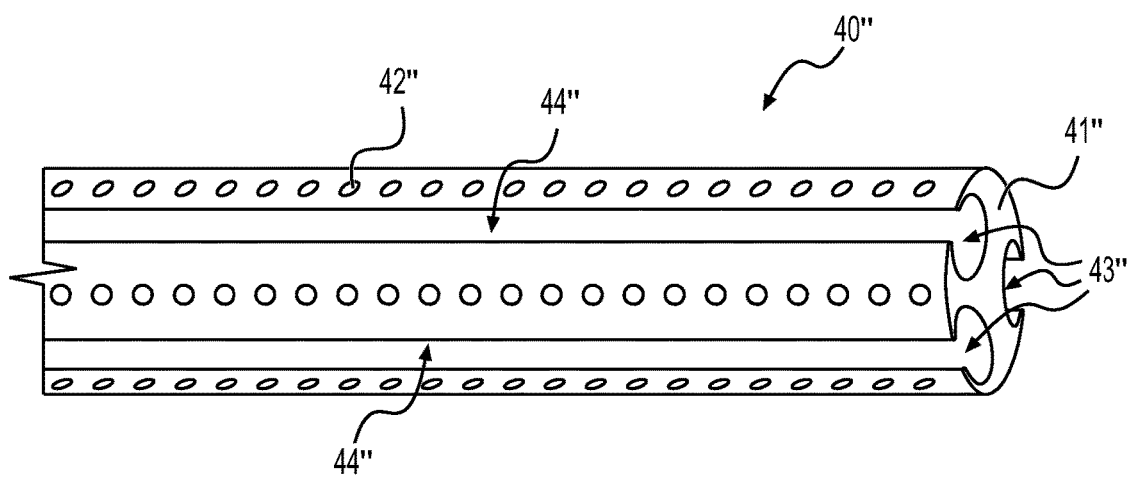
FIG. 2 is a side view of an embodiment of the SABLA catheter of the present invention.

FIG. 5 shows the junction 30, ETT 38, and catheter 40 in position within a patient. The ETT 38 is inserted to extend into the patient's trachea 70. The ventilator tubing 36 is connected to the junction 30 at connector 37 before or after insertion of the ETT 38. A single lumen catheter 40, such as shown in FIGS. 3A through 10A, may have ports 42, as shown in FIGS. 3A through 3D, or may be a simple tube, as shown FIGS. 9A and 9B. If the single lumen catheter 40 is a simple tube without ports, it may extend from the junction 26 at the control module 10, through the junction 30, and into the ETT 38 and trachea 70. If the catheter 40 has ports 42, or separate irrigation ports 42" and drainage channel side opening grooves 44" (as shown in FIG. 2 and discussed in more detail below), the catheter 40 may join an external tube 27, at a junction 29 (as shown in FIG. 5), in order to locate irrigation/lavage and drainage to the portions of the catheter 40 within the ETT 38 and the patient's trachea 70. The external tube 27 can extend through the seal 33 in the connector 31 at the junction 30 before after insertion of the ETT 38 into the trachea 70. The catheter 40 is then extended beyond the distal end 39 of the ETT 38 by one to two centimeters. The distal end 41 of the catheter 40 should be placed near (about one centimeter above) the carina 71, near the left 72 and right 73 main bronchi, so that it will evenly catch aspirates 78 from both left 74 and right 75 lungs.

Figure 3A:
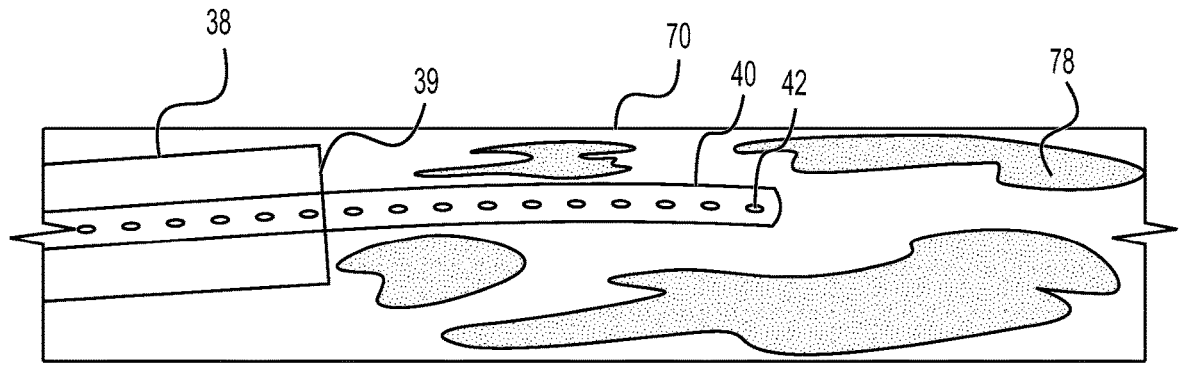
FIG. 3A shows a side view of an endotracheal tube and the SABLA catheter within a patient's trachea.
Figure 3B:
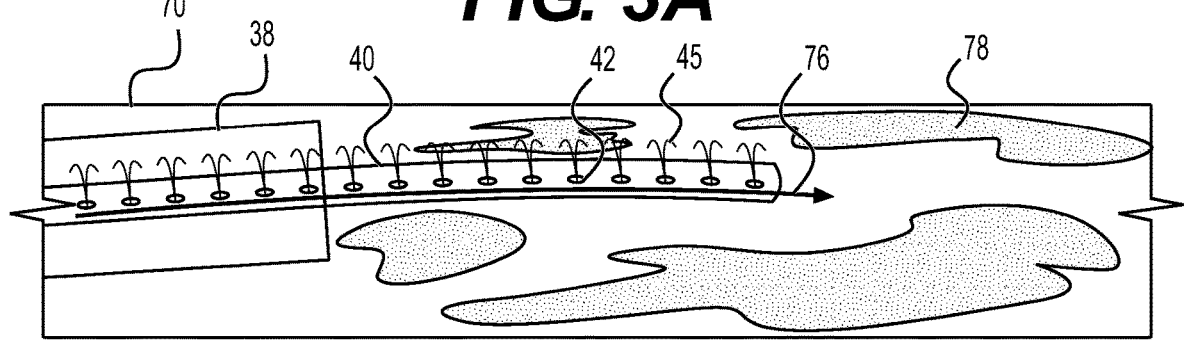
FIG. 3B shows a side view of the SABLA catheter dispersing lavage solution within a patient's trachea during inhalation.
Figure 3C:
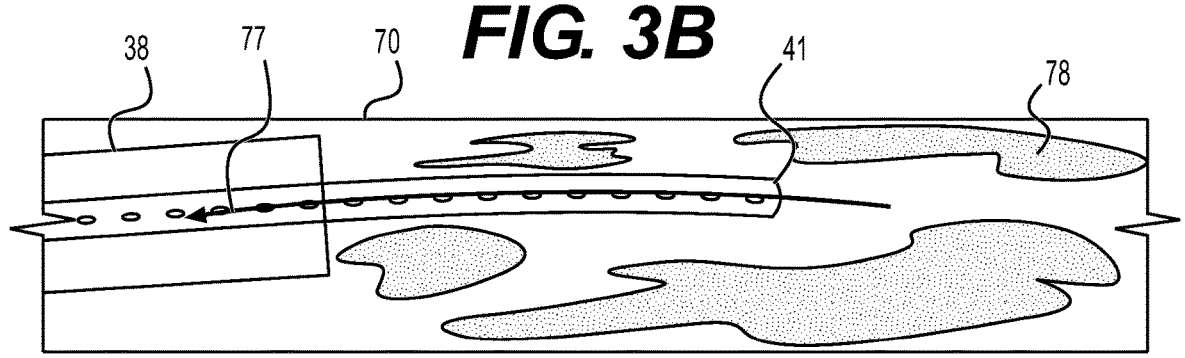
FIG. 3C shows a side view the SABLA catheter suctioning aspirates within a patient's trachea during exhalation.
Figure 3D:
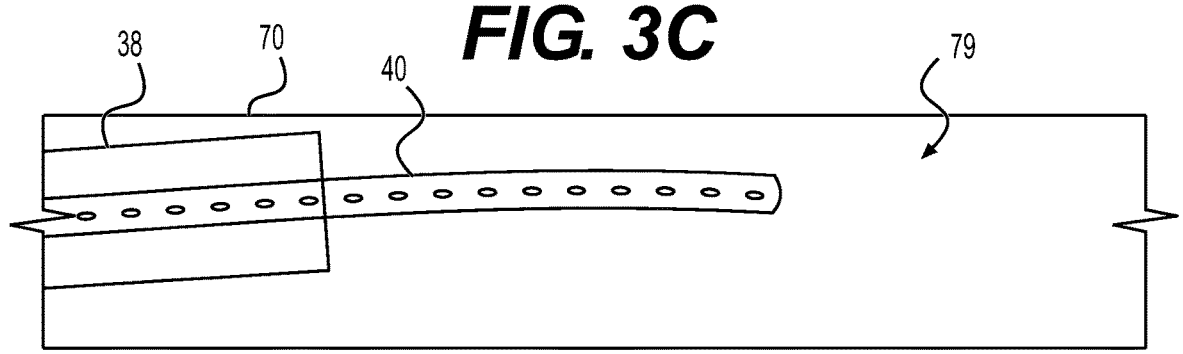
FIG. 3D shows a side view of the patient's trachea cleared of aspirates.

FIGS. 3A through 3D show the ETT 38 and catheter 40 placed within the trachea 70. In FIG. 3A, the ETT 38 has been placed in the trachea 70 and the catheter 40 has been extended beyond the end 39 of the ETT 38. Within the trachea 70, aspirates 78 have accumulated. During the inhalation cycle, indicated in FIG. 3B by arrow 76, irrigation solution 12 from the solution container 11 is pumped by the control module 10 through the catheter 40 (or through the external tube 27 and ported catheter 40), and dispersed 45 into the interior of the ETT 38 and trachea 70. During the exhalation cycle, indicated in FIG. 3C by arrow 77, the control module 10 synchronizes suction to remove aspirates 78 through the distal end 41 of the catheter 40 (or through both the distal end 41 of a ported catheter 40 and the ports 42), and pump them to the drainage container 17, thereby clearing the trachea 70 of aspirates 78, as shown in FIG. 3D.

Figure 10B:
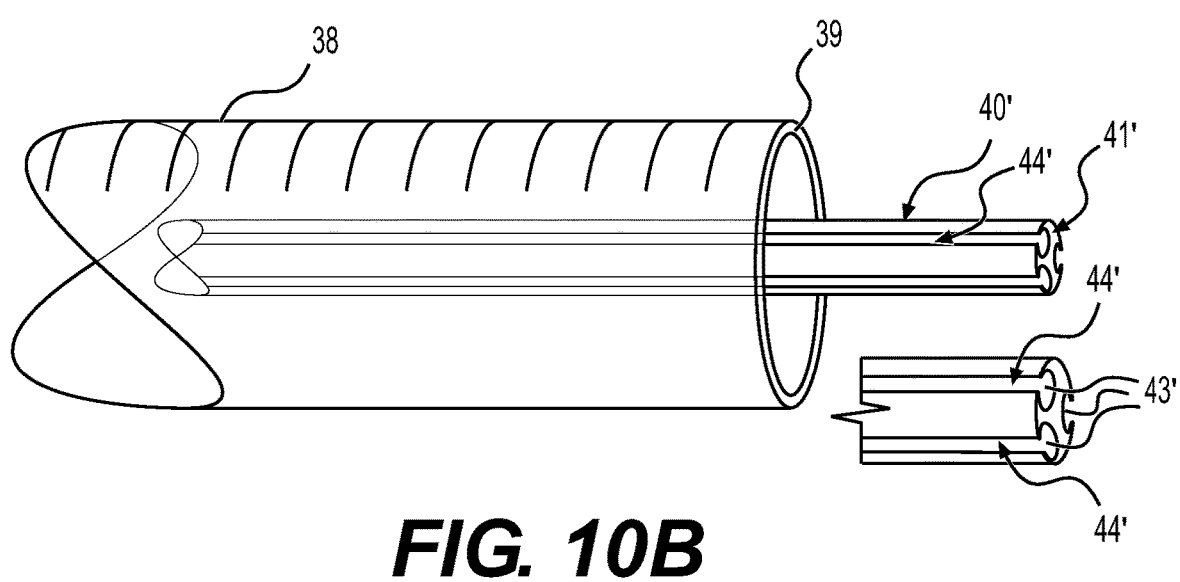
FIG. 10B shows a side view of an embodiment of the SABLA catheter within an endotracheal tube as well as an enlargement of the distal end of the catheter.
Figure 10C:
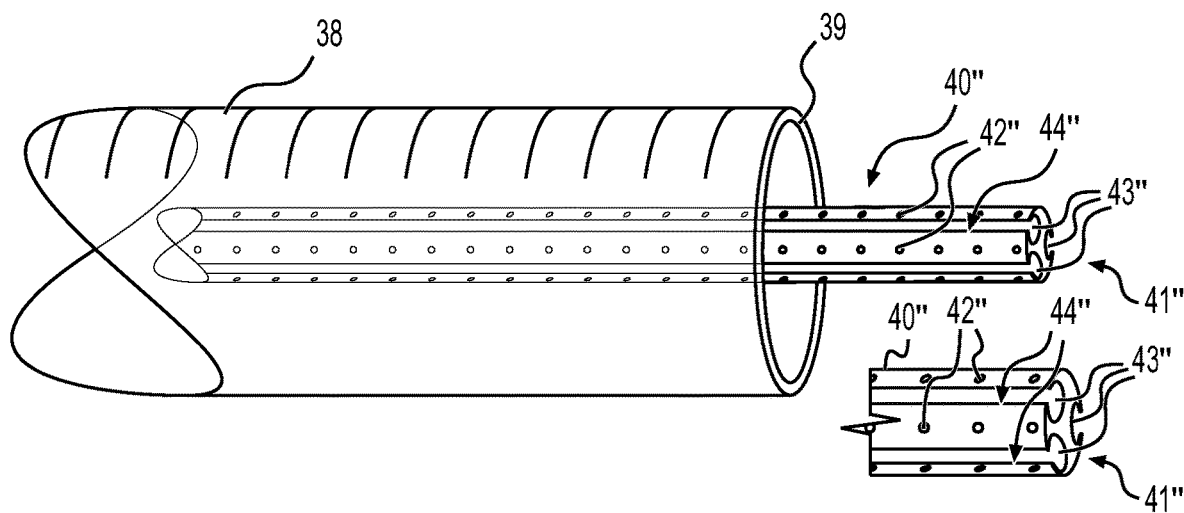
FIG. 10C shows a side view of an embodiment of the SABLA catheter within an endotracheal tube as well as an enlargement of the distal end of the catheter.
Figure 11:
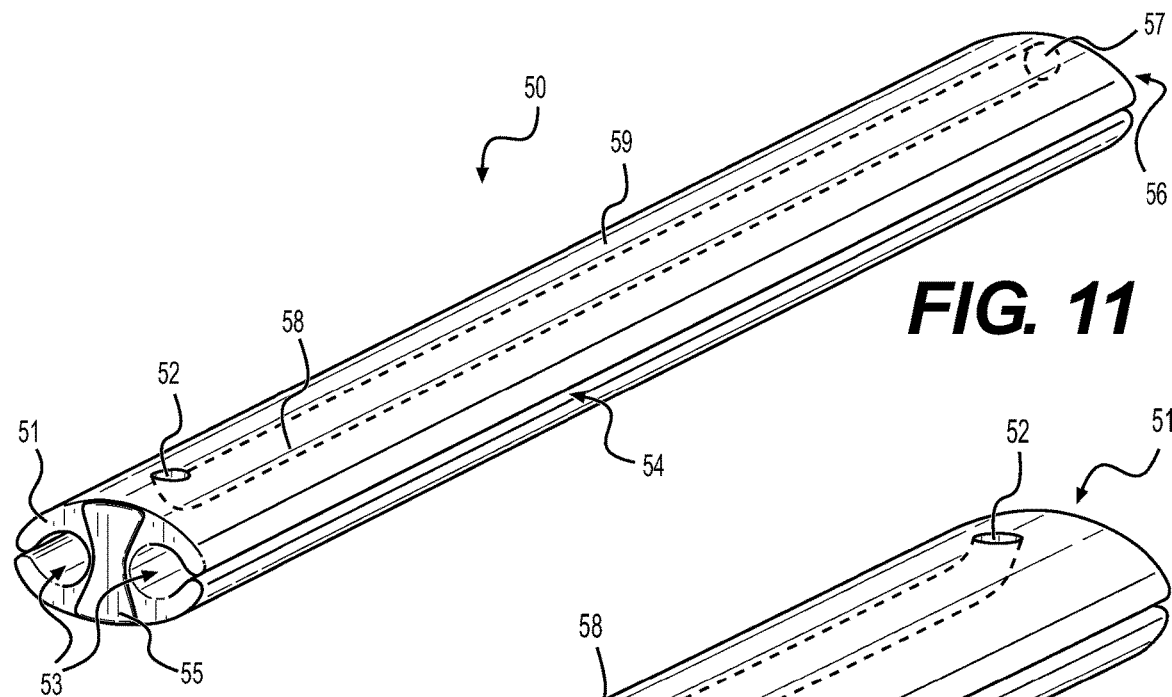
FIG. 11 shows a three-quarter perspective distal end view of a bi-channel embodiment of the SABLA catheter.
Figure 12:
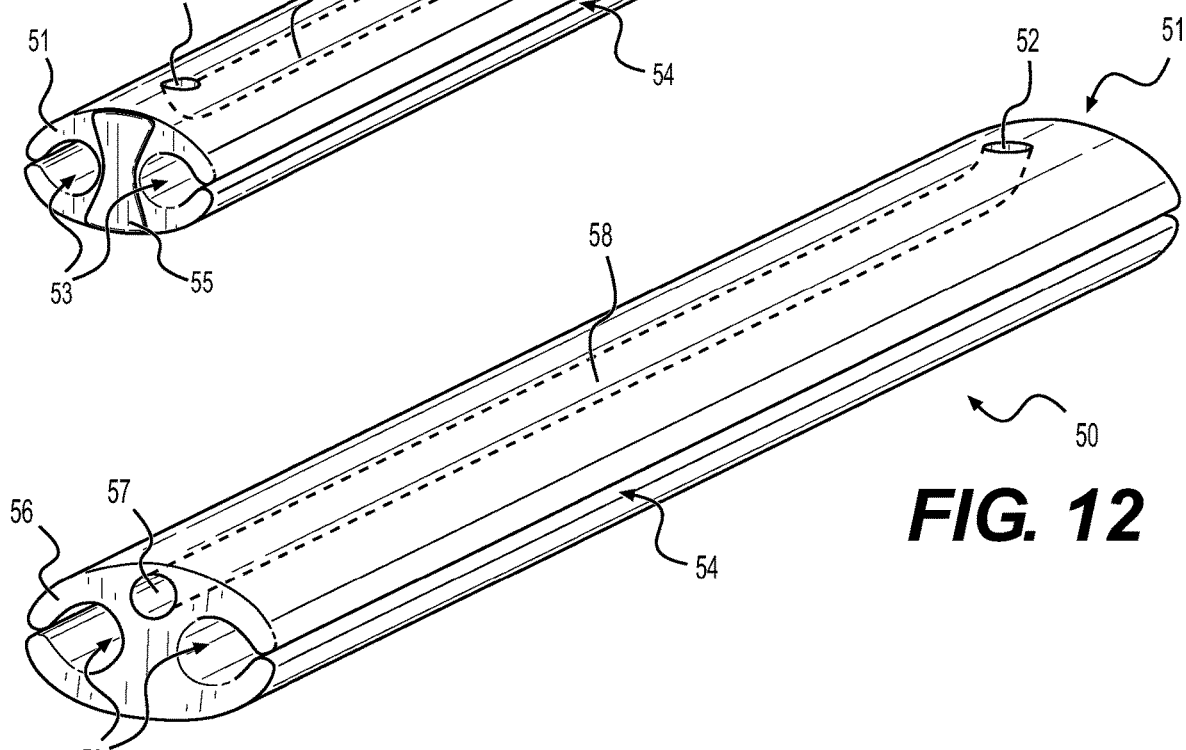
FIG. 12 shows a three-quarter perspective proximal end view of the bi-channel embodiment of the SABLA catheter.

FIGS. 2 and 10C show a preferred embodiment of the catheter 40" of the invention. The catheter 40" has multiple interior drainage channels 43" within the length of the catheter 40", similar to the drain described in U.S. Pat. No. 4,398,910 to Blake et al. ("Blake"). Side opening grooves 44" along the length of the catheter 40" communicate with the drainage channel 43". During the exhalation cycle, aspirates and other drainage 78 in the patient's trachea 70 or bronchi, 72 and 73, are drawn by suction, provided from and synchronized by the control module 10, through the side opening grooves 44" into the drainage channels 43" and transported back to the drainage container 17 (shown in FIG. 1). In addition, drainage 78 accumulated within the ETT 38 is also sucked through the channel grooves 44" and pumped back through the catheter 40" and external tube portion 27" (as shown in FIG. 17C) to the drainage container 17. The side opening grooves 44" will draw aspirates 78 into the drainage channels 43" over the extended length of the side opening grooves 44", thereby protecting the mucosal structure and avoiding pressure from being focused on a small area of the trachea 70 by a limited aperture, which can cause hyperemia or denudement of the epithelium. During the inhalation cycle, irrigation solution 12, pumped from and synchronized by the control module 10, is sprayed from irrigation ports 42" provided through the outside surface of the catheter 40". In the embodiment shown in FIG. 10C, a plurality of irrigation ports 42" are provided along the length of the catheter 40" between the drainage channel side opening grooves 44". The irrigation solution 12 provides moisture to the trachea 70 and bronchi, 72 and 73, to address the drying effect of the ventilator and to treat the accumulation and build up of aspirates in the trachea 70 and within the ETT 38. In addition, medicine, such as antibiotics, mucolytics, etc., may added to the irrigation solution 12 through the input port 13 at the solution container 11. The treated irrigation solution 12 can address common problems experienced by intubated patients. Because the provision of treated solution 12 is synchronized with the patient's inhalation and removal of aspirates and exudate drainage 78 is synchronized with exhalation, the need to remove an ETT 38 to treat the trachea 70 and bronchi, 72 and 73, is eliminated.

FIG. 10A shows an embodiment of a simplified catheter 40 of the present invention. The catheter 40 is a simple tube with an opening 43 at the distal end 41 and, optionally, ports 42 along its length. During the exhalation cycle, aspirates and other drainage 78 in the ETT 38 and the patient's trachea 70 or bronchi, 72 and 73, are drawn by suction, provided from and synchronized by the control module 10, through the distal opening 41 into the interior channel 43, as well as through the ports 42, if provided, and transported back to the drainage container 17 (shown in FIG. 1). During the inhalation cycle, irrigation solution 12, pumped from and synchronized by the control module 10, is provided to the trachea 70 and bronchi, 72 and 73, through the interior channel 43 and out the opening at the distal end 41 of the catheter 40, as well as through the ports 42, if provided.

FIG. 10B shows an alternative embodiment of the catheter 40'. The catheter's 40' synchronized drainage function is retained without integral irrigation. The catheter 40' has multiple irrigation and drainage channels 43' along the length of the catheter 40', similar to the drain described in the Blake patent. Side opening grooves 44' along the length of the catheter 40' communicate with the channels 43'. During the exhalation cycle, aspirates and other drainage 78 in the ETT 38 and the patient's trachea 70 or bronchi, 72 and 73, are drawn by suction, provided from and synchronized by the control module 10, through the side opening grooves 44' into the channels 43' and transported back to the drainage container 17 (shown in FIG. 1). During the inhalation cycle, irrigation solution 12, pumped from and synchronized by the control module 10, may be provided to the trachea 70 and bronchi, 72 and 73, through the channels 43' and out the side opening grooves 44' of the catheter 40'.

Figure 8A:
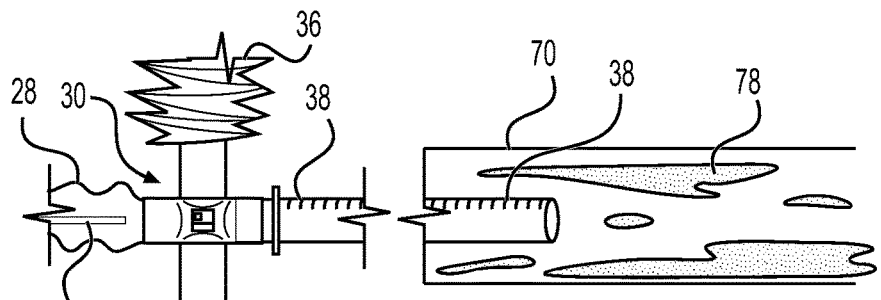
FIG. 8A shows a side view of the junction between the catheter and ventilator tubing as well as the endotracheal tube within a patient's trachea.
Figure 8B:
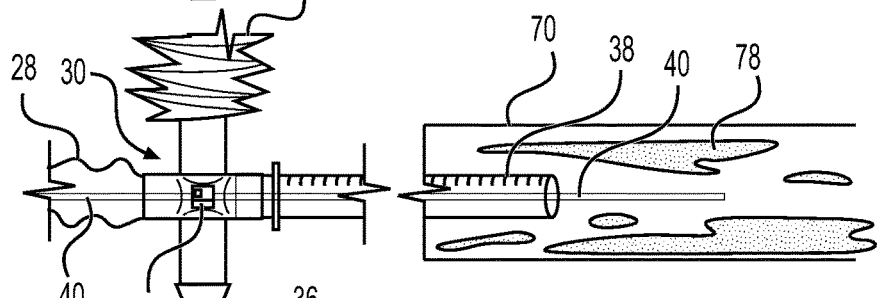
FIG. 8B shows a side view of the junction and the SABLA catheter exiting the endotracheal tube within the patient's trachea.
Figure 8C:
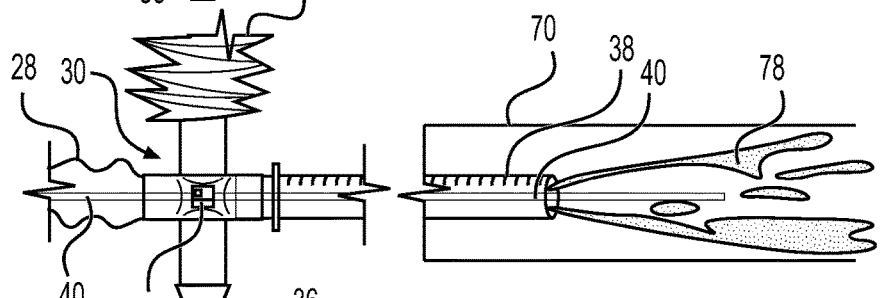
FIG. 8C shows a side view of the junction, the endotracheal tube, and the SABLA catheter clearing the airway of sputum and secretions during the exhalation cycle.
Figure 8D:
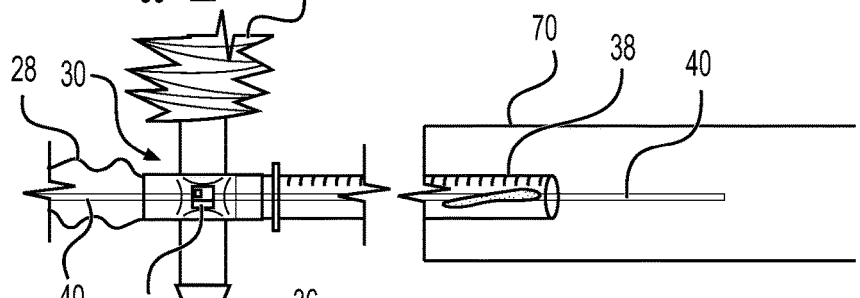
FIG. 8D shows a side view of the junction, the endotracheal tube, and the SABLA catheter completing clearance of sputum and secretions from the airway.
Figure 8E:
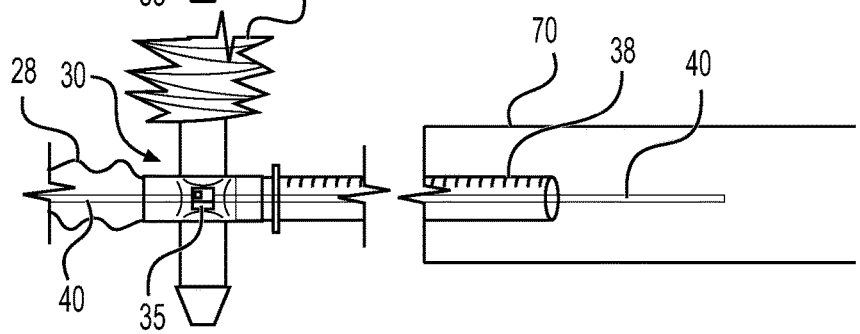
FIG. 8E shows a side view of the junction, the endotracheal tube, and the SABLA catheter having cleared the airway of sputum and secretions.

FIGS. 8A through 8E show the junction 30, with its connections to the ventilator tubing 36, the protective sheath 28 covering the catheter 40 and external tube portion 27, ETT 38, and pressure sensor 35, as well as the ETT 38 within a patient's trachea 70. In FIG. 8A, the ETT 38 has been inserted into the patient's trachea 70. Aspirates, sputum and other such drainage 78 have accumulated in the trachea 70. The catheter 40 has not yet been inserted through the junction 30 into the ETT 38. In FIG. 8B, the catheter has been inserted through the junction 30, into the ETT 38, and into the trachea 70. Typically, the catheter 40 is inserted one to two centimeters past the distal end (39 as shown in FIG. 3A) of the ETT 38, just short of the carina 71 (as shown in FIG. 9A). During inhalation, as sensed by the pressure sensor 35 (or by a conventional ventilator's pressure sensor), irrigation solution 12 is provided through the distal end 41 of the catheter 40, as well as through ports 42 (shown in FIGS. 3A through 3D). FIG. 8C shows the exhalation cycle, as sensed by the pressure sensor 35, during which the aspirates 78 are sucked from the trachea 70 into the distal end 41 and ports 42 of the catheter 40. FIG. 8D shows the remnants of the aspirates 78 being drown into the ports 42 of the catheter 40. FIG. 8E shows the trachea 70 and ETT 38 cleared of aspirates 78. The single-lumen catheter 40 shown in FIGS. 8A through 8E and the single-lumen ported catheter 40 shown in FIGS. 3A through 3D, illustrate how the catheter 40 of the present invention may be applied to the catheter embodiments, 40, 40', 40", or 50, in conjunction with a conventional ventilator to synchronize irrigation (as shown as 45 in FIG. 3A) with inhalation, as shown by arrow 76 in FIG. 3B, or drainage of aspirates 78 with exhalation, as shown by arrow 77 in FIG. 3C, or both.

FIG. 9A shows the catheter of the present invention, shown without embodiment detail (either 40, 40', 40", or 50), extending beyond the distal end 39 of the ETT 38. The distal end 41 of the catheter 40 extends one to two centimeters beyond the distal end 39 of the ETT 38, near the carina 71, where the left and right bronchi, 72 and 73, branch away to the left and right lungs, 74 and 75.

Figure 9B:
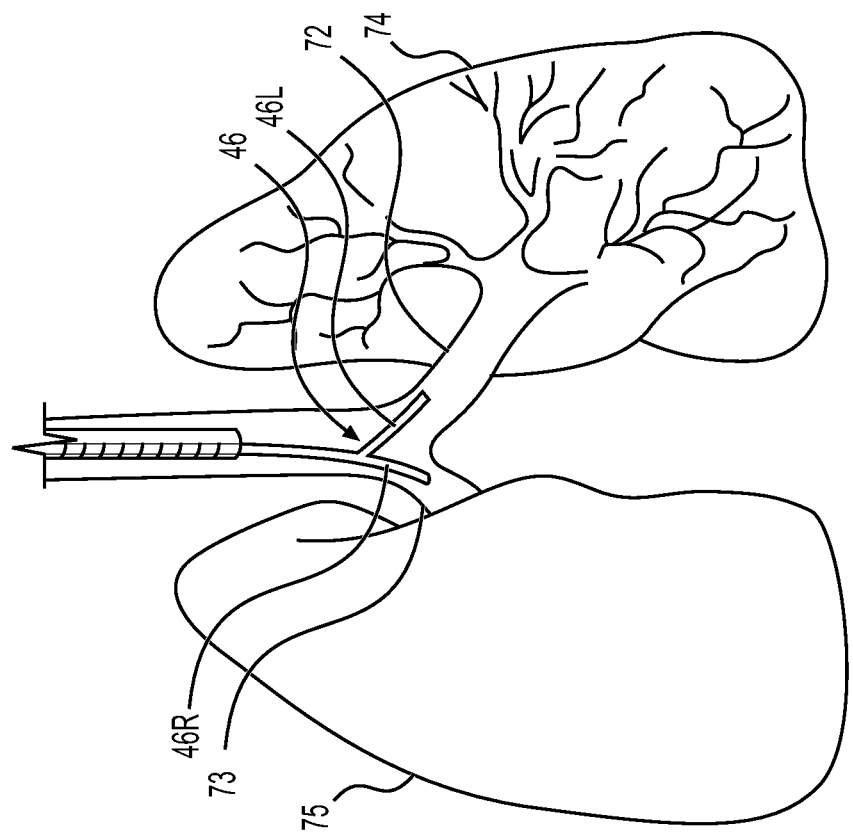
FIG. 9B show an alternative embodiment of the SABLA catheter within a patient's trachea and bronchi.
Figure 9A:
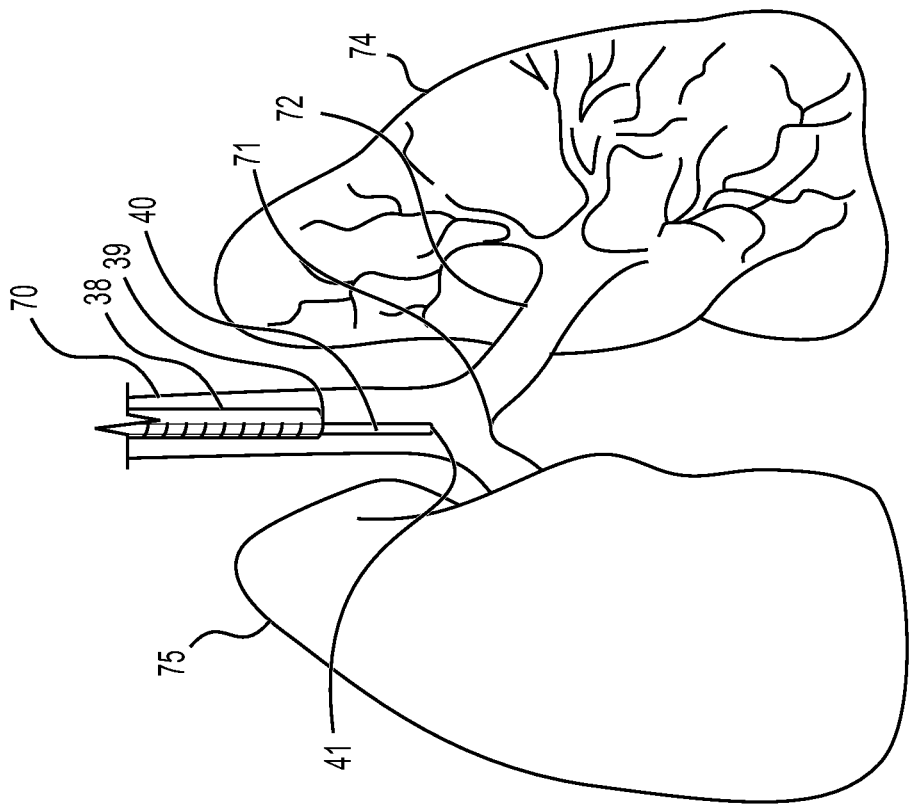
FIG. 9A shows an embodiment of the SABLA catheter within a patient's trachea and bronchi.

In an alternate embodiment of the invention, shown in FIG. 9B, the catheter 40 is branched 46. One branch 46L extends into the left main bronchus 72 and the other branch 46R extends into the right main bronchus 73. In this embodiment, both irrigation, through ports 42 (not shown in FIG. 9B) as well as through the distal ends of each branch, 46L and 46R, and drainage, through those ports 42 and distal ends, 46L and 46R, is simultaneously accomplished within both trachea and the left and right main bronchi, 72 and 73. By extending into the left and right main bronchi, 72 and 73, it is possible to suction aspirates that a catheter above the carina 71 will not reach.

Referring to FIGS. 11 through 15, a preferred embodiment of the invention, employing a bi-channel catheter 50, is a shown. Catheter 50 has a symmetrical oval cross section with two drainage channels 53 at opposite vertices along the main axis. As with the tri-channel catheter 40" described above, the drainage channels 53 communicate with side opening grooves 54 on the outer surface of the catheter 50 along at least a portion of the catheter's 50 length from the catheter proximal end 56 to the catheter distal end 51. During the exhalation cycle, sputum, aspirates and other drainage 78 in the ETT 38 and the patient's trachea 70 or bronchi, 72 and 73, are drawn by suction, provided from and synchronized by the control module 10, through the side opening grooves 54 into the drain channel 53 and transported back to the drainage container 17 (shown in FIG. 1). An irrigation port 52 is provided near the distal end 51 on a face 59 of the catheter 50. An irrigation supply duct 58 runs from the port 52 through the length of the catheter 50 to the a proximal end 56 of the catheter 50. During the inhalation cycle, irrigation solution 12, pumped from and synchronized with inhalation by the control module 10, runs through the external tube portion 27''', through the duct 58, and out the irrigation port 52 provided on the face 59 of the catheter 50 near its distal end 51. On the distal end 51 of the catheter 50, a radio-opaque marker is placed to make the catheter 50 more visible to X-rays, so that the catheter 50 may be located and correctly positioned within the patient's trachea 70, about one centimeter from the carina 71.

Figure 13:
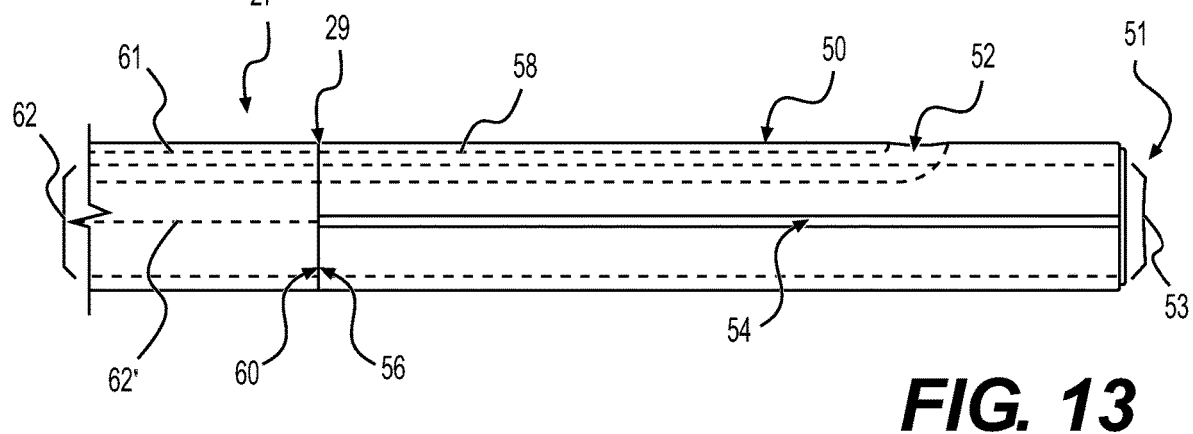
FIG. 13 shows a side view of the bi-channel embodiment of the SABLA catheter connected to an external tube.
Figure 14:
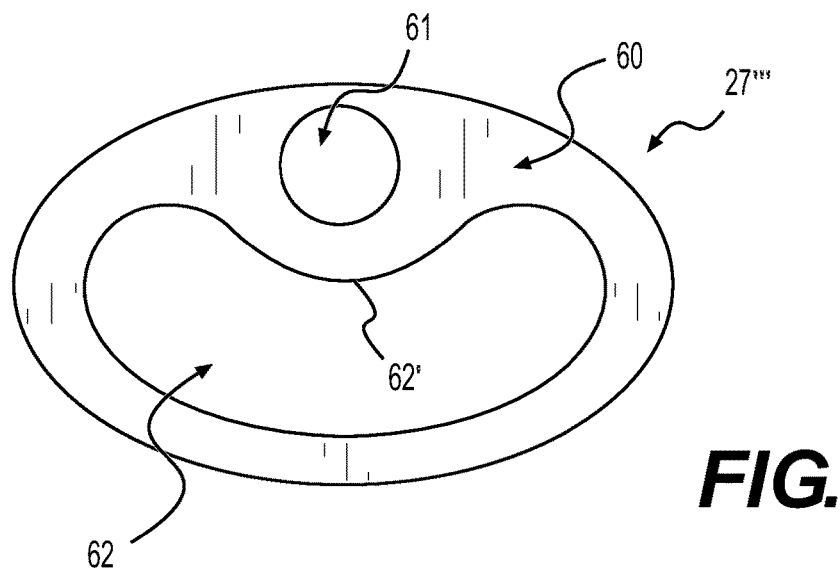
FIG. 14 shows a distal end view of the external tube for the bi-channel embodiment of the SABLA catheter.
Figure 15:
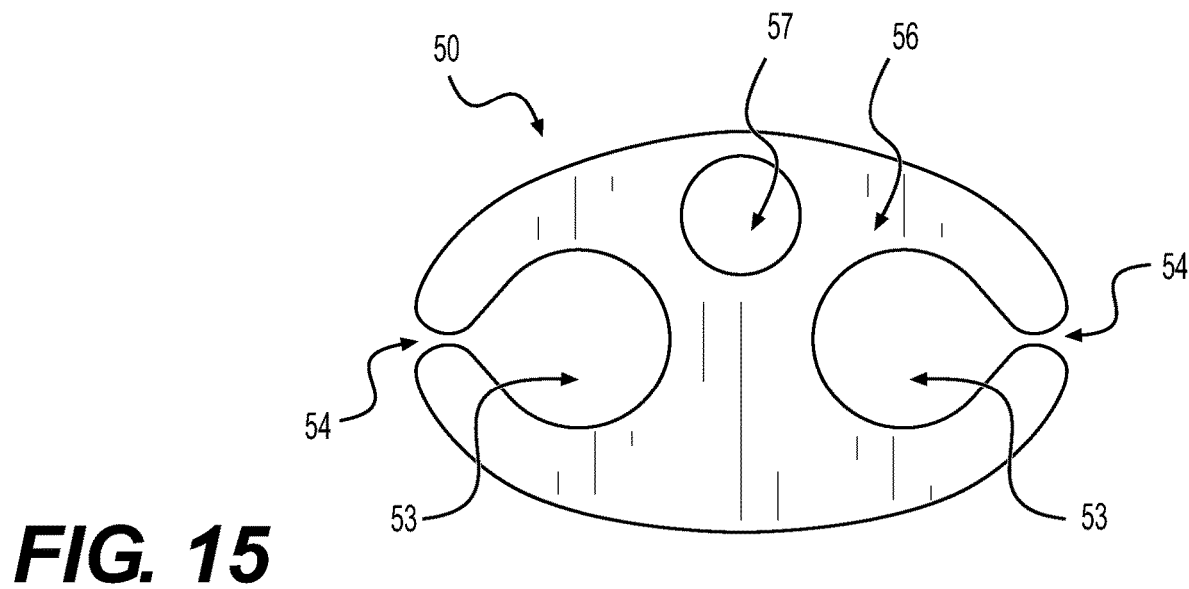
FIG. 15 shows a proximal end view of the bi-channel embodiment of the SABLA catheter.

FIGS. 13 through 15 show the junction 29 at the proximal end 56 of the bi-channel catheter 50 and the distal end 60 of the complimentary bi-channel external tube 27'''. The external tube 27''' extends back from or through the seal 33 of the junction 30 (shown in FIGS. 5 and 7) to the control module 10 (shown in FIG. 1). At junction 29 the two drainage channels 53 at the proximal end 56 the catheter 50 join the drainage duct 62 at the distal end 60 of the external tube 27'''.

Figure 19:
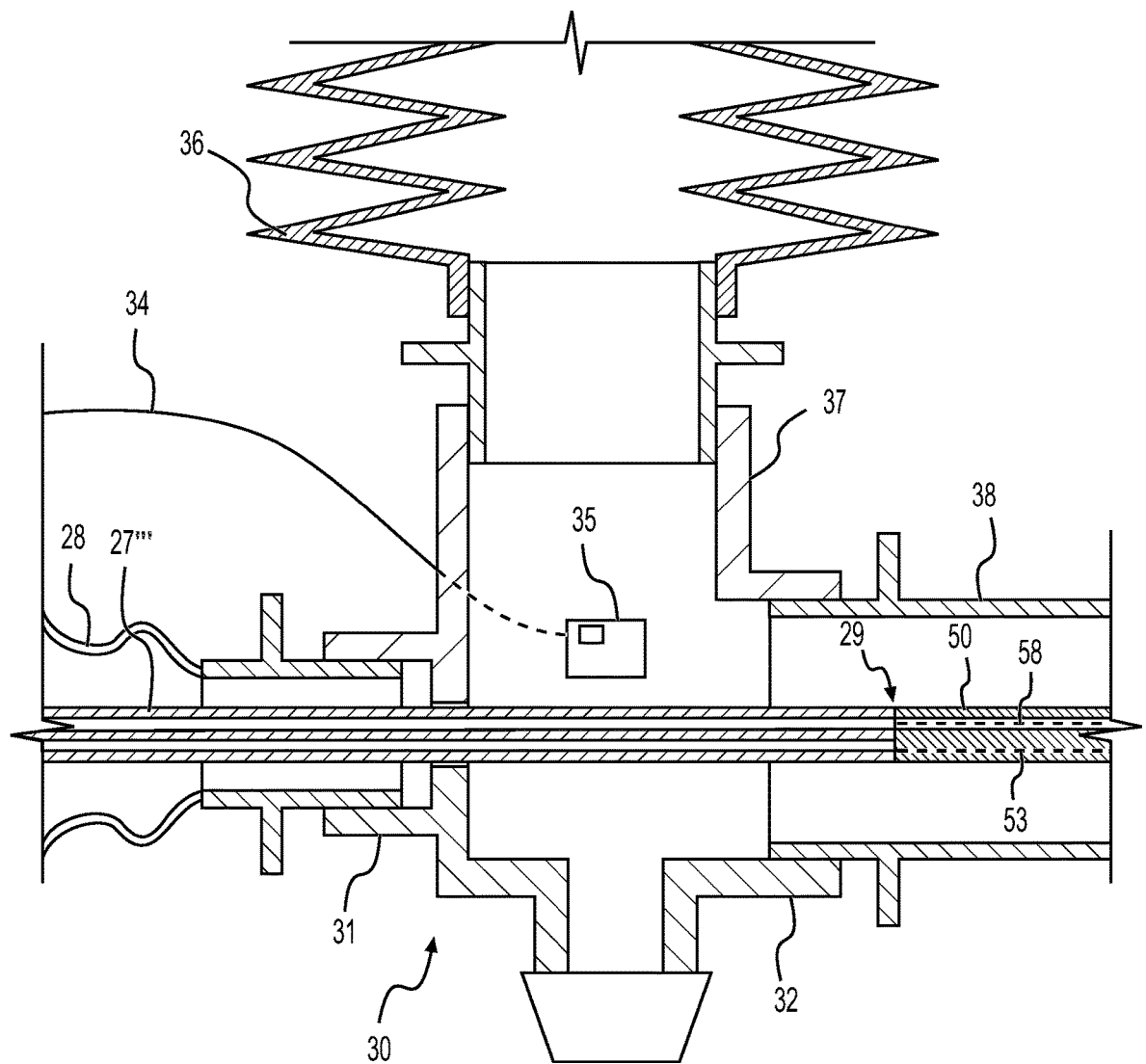
FIG. 19 shows a block diagram of the junction of the external tube/catheter, ventilator tubing, and endotracheal tube and catheter of the SABLA apparatus.

In the embodiment shown in FIGS. 13, 14 and 19, the drainage duct 62 is in a bent oval or wiener shape, with the dip in the upper part of the duct 62 indicated at 62'. Other shapes for one or more passages of the drainage duct 62 are possible, such as, for example, a pair of circular ducts corresponding with the nearly circular channels 53, or a single duct in the external tube 27''' that bifurcates to join the pair of drainage channels 53 of the bi-channel catheter 50. During the exhalation cycle, suction from the control module 10 draws aspirates 78 from the trachea 70 and interior of the ETT 38 through the catheter's drainage channel 53 openings at the distal end 51 of the catheter 50, as well as through the side opening grooves 54, into the drainage channels 53. These aspirates 78 are then sucked into the drainage duct 62 of the external tube 27''' and carried through the external tube 27''' to the junction 26 at the control module 10. From junction 26 the aspirates 78 from the external tube 27''' are routed to the drainage intake 18 and deposited into the drainage container 17.

Similarly, at junction 29 between the catheter 50 and the external tube 27''', the irrigation duct opening 57 at the proximal end 56 of the catheter 50 joins the irrigation solution duct 61 at the distal end 60 of the external tube 27'''. During the inhalation cycle, irrigation solution 12, as well as any medication added to the solution 12, is pumped from the control module 10 through the pumping conduit 15 to junction 26 and into the irrigation duct 61 of the external tube 27'''. At junction 29, the irrigation solution 12 continues into the interior channel 58 of the catheter 50 and exits through the irrigation port 52 into the interior of the ETT 38 or the trachea 70.

Figure 16A:
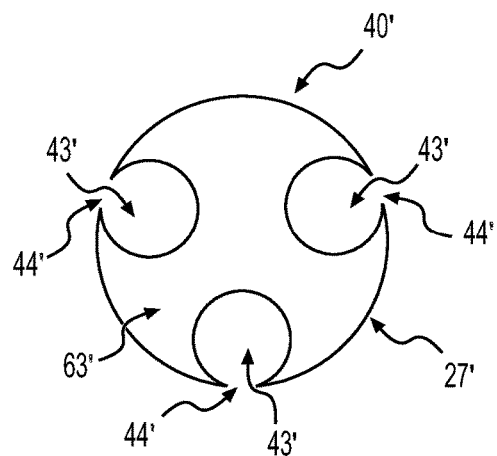
FIG. 16A shows the proximal end view of a tri-channel embodiment of the SABLA catheter without irrigations ports.
Figure 16B:
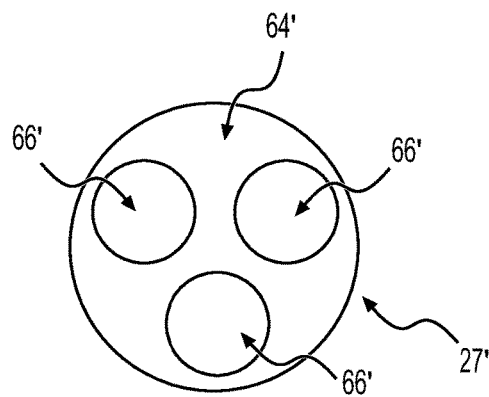
FIG. 16B shows the distal end view of the external tube for the tri-channel embodiment of the SABLA catheter without irrigations ports.

FIGS. 16A and 16B show end views of the 3-channel catheter 40' and its complimentary 3-channel external tube 27'. At junction 29 between the catheter 40' and the external tube 27', the three channels 43' of the catheter 40' join ducts 66' at one end 64' of the external tube 27'. The external tube 27' ducts 66' and the channels 43' may be used exclusively for drainage or irrigation or for both drainage and irrigation. Alternatively, the external tube 27' may employ a single drainage duct 66' that communicates with the channels 43' of the 3-channel catheter 40'. During the exhalation cycle, suction from the control module 10 draws aspirates 78 from the trachea 70 and interior of the ETT 38 through the catheter's channel openings 43' and through the side opening grooves 44'. These aspirates 78 are then sucked into the ducts 66' of the external tube 27' and carried through the external tube 27' to the junction 26 at the control module 10. From junction 26 the aspirates 78 are routed to the drainage intake 18 and deposited into the drainage container 17. As with the single-lumen portless catheter 40, described above, it will be appreciated that channels 43' could also be employed to supply irrigation solution 12 to the interior of the ETT 38 and trachea 70, as synchronized by the control module 10 with the inhalation cycle.

Figure 17A:
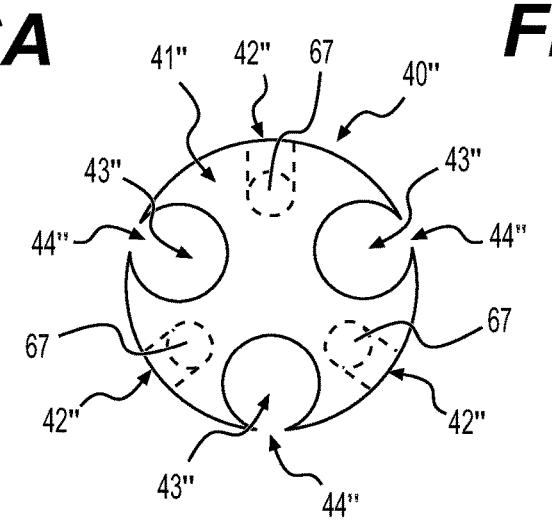
FIG. 17A shows the distal end view of an alternative tri-channel embodiment of the SABLA catheter with irrigations ports.
Figure 17B:
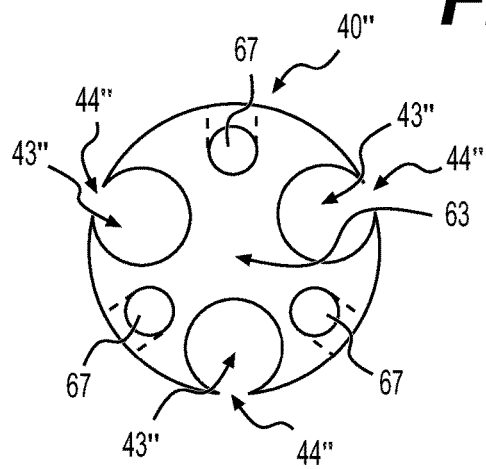
FIG. 17B shows the proximal end view of the alternative tri-channel embodiment of the SABLA catheter with irrigations ports.
Figure 17C:
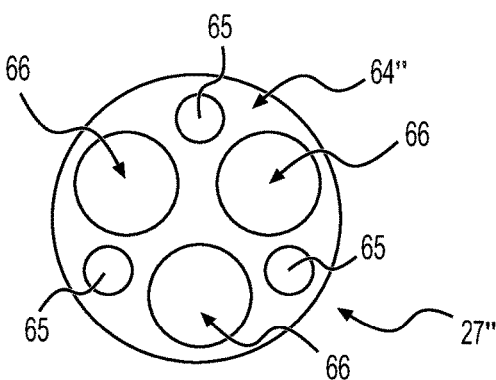
FIG. 17C shows the distal end view of an external tube for the alternative ti-channel embodiment of the SABLA catheter with irrigations ports.

FIGS. 17A through 17C show distal (FIG. 17A) and proximal (FIG. 17B) end views of the 3-channel catheter 40" and its complimentary 3-channel external tube 27" (FIG. 17C). At junction 29 between the proximal end 63 of the catheter 40" and the distal end 64" of the external tube 27", the three drainage channels 43" of the catheter 40" join drainage ducts 66. During the exhalation cycle, suction from the control module 10 draws aspirates 78 from the trachea 70 and interior of the ETT 38 through the catheter's drainage channel 43" openings at the distal end 41" of the catheter 40", as well as through the side opening grooves 44", into the drainage channels 43". From junction 26 at the control module 10, the aspirates 78 are routed to the drainage intake 18 and deposited into the drainage container 17.

Similarly, at junction 29 the irrigation duct openings 67 at the proximal end 63 of the catheter 40" join the irrigation solution ducts 65 at the distal end 64" of the external tube 27". During the inhalation cycle, irrigation solution 12, as well as any medication added to the solution 12, is pumped from the control module 10 through the pumping conduit 15 to junction 26 and into the irrigation ducts 65 of the external tube 27". At junction 29, the irrigation solution 12 continues into the interior channels 67 of the catheter 40" and exits through the irrigation ports 42" into the interior of the ETT 38 or the trachea 70.

Figure 18:
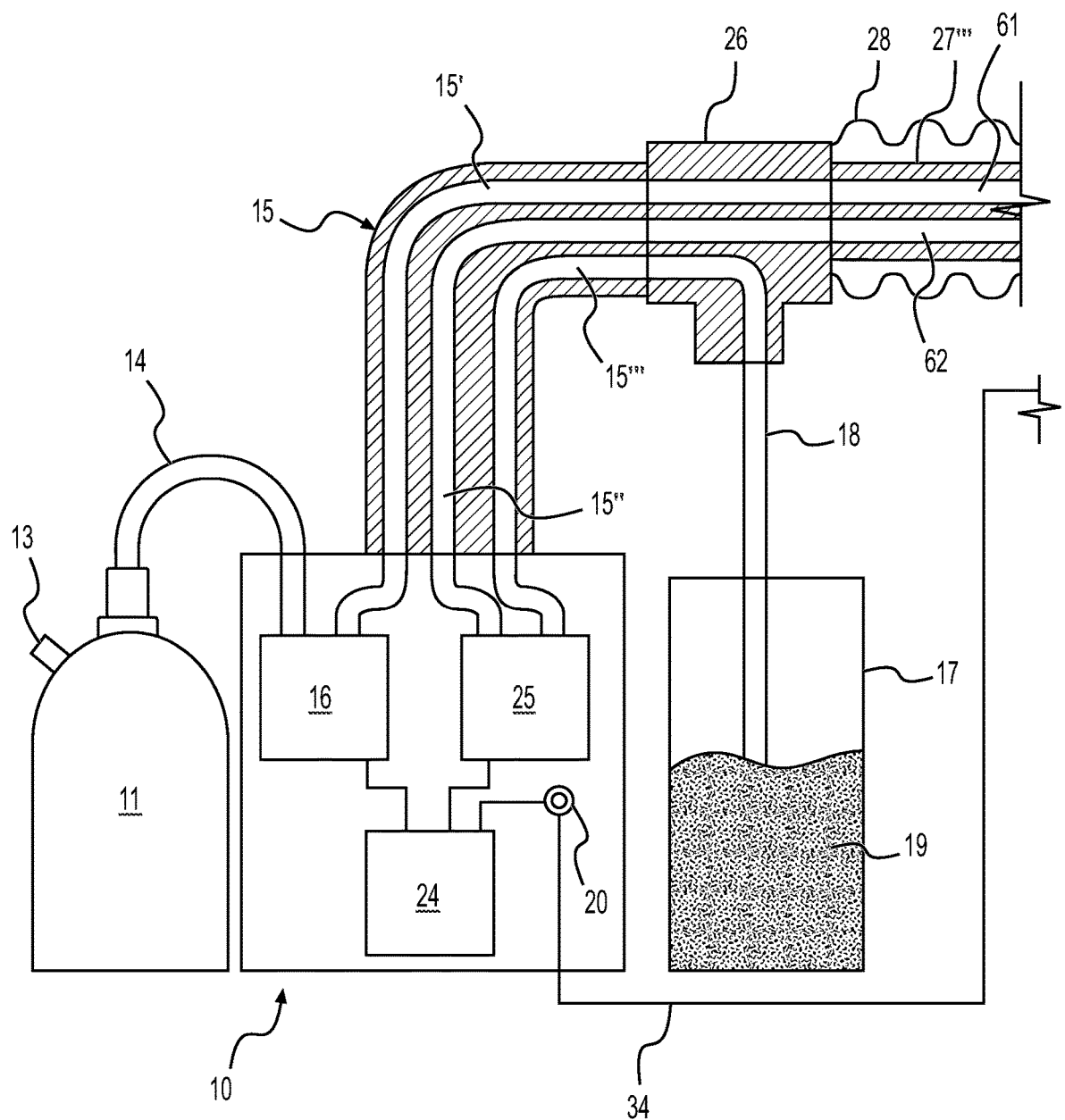
FIG. 18 shows a block diagram of the components of the control module of the SABLA apparatus.

Referring to FIGS. 18 and 19, the control module 10 and junction 30 between the external tube (the bi-channel external tube 27''' is shown), ventilator tubing 36, and ETT 38 and catheter 50 are shown. During the exhalation cycle, sputum, aspirates and other drainage 78 in the ETT 38 and the patient's trachea 70 or bronchi, 72 and 73, are drawn by suction from a n electrically powered drainage pump 25 via drainage conduit 15", external tube drainage duct 62, and catheter 50 drainage channels 53. The pump's 25 suction is synchronized with the patient's exhalation, as detected by pressure sensor 35, which may be the ventilator's pressure sensor (not shown) or may be a separate pressure sensor in a location where exhalation and inhalation may be detected, such as within the ETT 38 or the junction 30, as shown in FIG. 19. The pressure sensor 35 senses the positive pressure of exhalation and sends an exhalation pressure signal via a communication link 34, such as a wire or wireless link, to the pressure sensor input 20 of control module 10 and then to the control processor 24. The control processor 24 recognizes the signal from the pressure sensor 35 as indicative of positive pressure in the ETT 38 and can direct the drainage pump 25 to establish negative pressure through drainage conduit 15" to the drainage duct 62 within the external tube 27''' and, thereby, the drain channels 53 and side opening grooves 54 of the catheter 50. This suction draws sputum, aspirates and other drainage 78 in the ETT 38 and the patient's trachea 70 or bronchi, 72 and 73, into the drain channels 53, to the drainage duct 62 of the external tube 27''', and then into the drainage conduit 15", where the drainage is then sent by pump 25 through drainage outflow conduit 15''' to drainage intake 18 and into drainage container 17. When the pressure sensor 35 detects a change from positive pressure, associated with exhalation, to negative pressure, associated with inhalation, the pressure sensor 35 sends an inhalation pressure signal via the communication link 34 to the pressure sensor input 20 of control module 10 and then to the control processor 24. The inhalation pressure signal is analyzed by the control processor 24, which can determine when the drainage pump 25 should cease negative pressure through drainage conduit 15", drainage duct 62 within the external tube's 27''', and drain channels 53 and side opening grooves 54 of the catheter 50.

During the inhalation cycle, irrigation solution 12, as well as any medicine that may have been added to the irrigation solution container 11 through medication port 13, is pumped by an electrically powered irrigation pump 16 from the irrigation container 11 through supply pipe 14 to the irrigation fluid conduit 15', external tube's 27''' irrigation solution duct 61, catheter 50 irrigation supply interior duct 58, and out the irrigation port 52 into the interior of the ETT 38, trachea 70, and bronchi, 72 and 73. The irrigation pump 16 is synchronized with the patient's inhalation, as detected by a pressure sensor 35, which may be the ventilator's pressure sensor (not shown) or may be a separate pressure sensor 35 in a location where the patient's inhalation may be detected, such as within the ETT 38 or the junction 30, as shown in FIG. 19. The pressure sensor 35 senses the negative pressure of inhalation and sends an inhalation pressure signal via the communication link 34, such as a wire or wireless link, to the pressure sensor input 20 of control module 10 and then to the control processor 24. The control processor 24 directs the irrigation pump 16 to pump irrigation solution 12, as described above. When the pressure sensor 35 detects a change from negative pressure, associated with inhalation, to positive pressure, associated with exhalation, the pressure sensor 35 will send an exhalation pressure signal, which is received by the control processor 24, which will analyze the signals and can direct the irrigation pump 16 to cease positive pressure through irrigation fluid conduit 15', irrigation solution duct 61 within the external tube's 27''', and irrigation supply duct 58 of the catheter 50.

The control processor 24 recognizes the inhalation and exhalation pressure signals received from the pressure sensor 35, analyzes them (e.g., for duration, strength, consistency, etc.), synchronizes operation of the irrigation pump 16 with inhalation and drainage pump 25 with exhalation (or controls a single pump operating as both the drainage and irrigation pump), and controls the frequency, strength and duration of lavage and aspiration. Typically, a three-to-one ratio of seconds of inhalation to exhalation is observed in a patient receiving ventilation. The control processor 24 will analyze the pressure signals received from the pressure sensor 35 to synchronize the duration of lavage with saline solution and medicine from the irrigation container 11 with inhalation, as well as control the timing, frequency, duration and pressure strength of drainage suction with exhalation. Further, it is common for patients requiring ventilation to arrive with significant mucous accumulation ("wetter" lungs), requiring more frequent or prolonged suctioning. For example, the control processor could direct the drainage pump 25 to provide suction after every other inhalation cycle. Similarly, mucous can build up and become more viscous, requiring more frequent lavage to break up the mucous and avoid clogging the drainage channels (43, 43', 43", 53) or ports (42). A keypad 21 on the control module 10 allows a technician to program the control processor 24 to perform drainage and irrigation according to predetermined parameters, such as frequency, duration, intervals, and pumping strength. The control processor 24 can be programmed to direct the frequency of drainage and irrigation (e.g., drainage after every other inhalation cycle and irrigation after every sixth exhalation cycle), duration of drainage and irrigation (e.g., drainage for fifteen minutes and irrigation for five minutes), intervals (e.g., drainage and irrigation at the specified frequencies and durations every third hour), and pumping strength for suction by the drainage pump 25 and irrigation by the irrigation pump 16 (e.g., suction pressure at 50 mmHg and irrigation solution volume of 7 cc per inhalation cycle). In addition, the aspirates 78 received by the drainage pump 25 may be analyzed for opacity, color, viscosity, etc., in the control module 10 or in drainage container 17, and the control processor 24 can alert the technician to these indicators of potential problems by displaying the analysis on the control module's 10 screen 22 or issuing a sound alert from a speaker 23 or both. In this way, the present invention automates and synchronizes the process of inspiration and aspiration of a mechanical ventilator, which has heretofore been performed manually by technicians. Because the present invention can perform irrigation and drainage automatically and more precisely synchronized with inhalation and exhalation, the demands imposed on medical staff are reduced. The reduction of manual labor time spent on aspiration and lavage is a critical issue when medical staff are overwhelmed by unusually high demand, such as during the current COVID-19 pandemic and in natural disasters and in military hospitals receiving many seriously injured patients within short period of time.

As the ventilator and patient cycle through inhalation and exhalation, the SABLA control module 10 synchronizes lavage with irrigation fluid 12 during inhalation and drainage of aspirate 78 during exhalation. The control module 10 will also synchronize and automate the volume, strength and frequency of irrigation and suction to adjust for thick and tenacious secretions, which require stronger or more frequent drainage or irrigation (e.g., strong, moderate, or maintenance modes). The control module 10 can monitor and track clinical parameters of the aspirates 78 received at the control module 10 as drainage 19, including drainage volume, clarity, viscosity, and tenacity, etc. The control module 10 can analyze these clinical parameters of the drainage 19 to determine the status of the patient and adjust the predetermined parameters discussed above, as well as medication to be added to the irrigation solution 12. Information about the drainage 19 volume and content may displayed on the screen 22 of the control module 10. In addition, the drainage container 17 may be transparent to allow tracheo-bronchial aspirates 78 to be seen, which will provide information about the patient's condition. The drainage 19 may also be sent for cultures, cytology, cell counts, and other laboratory analysis and, depending on the analysis of the drainage 19, the clinical parameters, including the use of medicines in the irrigation solution 12, may downloaded to the control processor 24 which can, in turn, display recommendations on the screen 22 of the control module 10. The ease and availability of Pharmaco-therapeutic medicines (antibiotics, antivirals, mucolytics, steroid, etc.) addition to saline irrigation enhances the clinical efficacy of irrigation. The invention will decrease infection, reduce ventilation duration, cut healthcare costs, and eliminate morbidity/mortality. Because the SABLA invention works in a closed system, it protects staff from pathogens (i.e., Sars-CoV2).

The drawings and description set forth here represent only some embodiments of the invention. After considering these, skilled persons will understand that there are many ways to make a synchronized automated bronchial lavage aspiration apparatus according to the principles disclosed. The inventors contemplate that the use of alternative structures, materials, or manufacturing techniques, which result in a synchronized automated bronchial lavage aspiration apparatus according to the principles disclosed, will be within the scope of the invention.

The invention claimed is:

1. A synchronized automated bronchial lavage aspiration apparatus comprising:
    a drainage pump and a drainage conduit extending from the drainage pump,
    a catheter having a catheter proximal end, a catheter distal end, a catheter length between the catheter proximal end and the catheter distal end, a catheter outer surface along the catheter length, and an interior channel within the catheter outer surface in fluid communication at the catheter proximal end with the drainage conduit, said interior channel having at least one opening proximal to the catheter distal end,
    a pressure sensor sensing positive pressure associated with exhalation and negative pressure associated with inhalation, wherein the pressure sensor generates an exhalation pressure signal responsive to the positive pressure associated with exhalation, and
    a control processor configured to receive the exhalation pressure signal from the pressure sensor over a communication link from the pressure sensor, wherein the control processor synchronizes and automates suction by the drainage pump according to predetermined drainage parameters in response to the positive pressure associated with exhalation,
    wherein said suction draws aspirates from the at least one opening into the interior channel and into the drainage conduit,
        wherein said predetermined drainage parameters include drainage frequency, drainage duration and drainage interval.

2. The synchronized automated bronchial lavage aspiration apparatus of claim 1, further comprising:
    an irrigation pump and an irrigation conduit extending from the irrigation pump,
    wherein the interior channel is in fluid communication at the catheter proximal end with the irrigation conduit,
    the pressure sensor further generating an inhalation pressure signal responsive to the negative pressure associated with inhalation, and
    wherein the control processor further synchronizes and automates pumping irrigation solution from the irrigation pump according to a predetermined irrigation parameters through the irrigation conduit and the interior channel and out the at least one opening of the catheter in response to receiving the inhalation pressure signal associated with inhalation, and wherein said predetermined irrigation parameters include irrigation frequency, irrigation duration, irrigation volume and irrigation interval.

3. The synchronized automated bronchial lavage aspiration apparatus of claim 2, wherein the aspirates suctioned by the drainage pump into the drainage conduit are received at a control module and analyzed by the control processor for clinical parameters including aspirate volume, aspirate clarity, aspirate viscosity, and wherein the control processor adjusts the predetermined drainage parameters and the predetermined irrigation parameters in response to the clinical parameters.

4. The synchronized automated bronchial lavage aspiration apparatus of claim 3, wherein the control module further comprises a screen to display the predetermined drainage parameters, the predetermined irrigation parameters, and the clinical parameters, and wherein the control module further comprises a keypad to input directions to the control processor to adjust the predetermined drainage parameters and the predetermined irrigation parameters.

5. The synchronized automated bronchial lavage aspiration apparatus of claim 4, wherein the control processor displays on the screen recommended medication to be added to the irrigation solution in response to the clinical parameters analyzed by the control processor.

6. The synchronized automated bronchial lavage aspiration apparatus of claim 2, wherein the at least one opening through the catheter further comprises a plurality of ports through the catheter outer surface.

7. The synchronized automated bronchial lavage aspiration apparatus of claim 2, wherein the at least one opening through the catheter is formed by a side opening groove along at least a portion of the catheter length in the catheter outer surface.

8. The synchronized automated bronchial lavage aspiration apparatus of claim 2, further comprising:

an external tube containing the drainage conduit and irrigation conduit and joining the catheter proximal end, and a junction with a ventilator connector to receive a ventilation tube from a ventilator, a catheter connector to receive the external tube and catheter, and an ETT connector to receive an endotracheal tube, wherein the ventilator, catheter and ETT connectors of the junction admit to a common enclosed space, and wherein the catheter and ETT connectors are oriented to allow the external tube and catheter to pass into and out of the endotracheal tube.

9. The synchronized automated bronchial lavage aspiration apparatus of claim 8, further comprising a junction pressure sensor in communication with the common enclosed space to sense pressure within the endotracheal tube associated with exhalation and inhalation and to generate the exhalation pressure signal and the inhalation pressure signal and to transmit the exhalation pressure signal and the inhalation pressure signal through the communication link to the control processor.

10. The synchronized automated bronchial lavage aspiration apparatus of claim 9, wherein the communication link to the control processor is a wire.

11. The synchronized automated bronchial lavage aspiration apparatus of claim 9, wherein the communication link to the control processor is a wireless connection.

12. The synchronized automated bronchial lavage aspiration apparatus of claim 1, wherein the at least one opening through the catheter is formed by a side opening groove along at least a portion of the catheter length in the catheter outer surface.

13. The synchronized automated bronchial lavage aspiration apparatus of claim 1, further comprising:

an irrigation pump and an irrigation conduit extending from the irrigation pump, an irrigation channel within the catheter and fluidly separated from the interior channel, wherein the irrigation channel is in fluid communication at the catheter proximal end with the irrigation conduit, and wherein the irrigation channel is in fluid communication with an irrigation port through the catheter outer surface proximal to the catheter distal end, the pressure sensor further generating an inhalation pressure signal responsive to the negative pressure associated with inhalation, and wherein the control processor further synchronizes and automates pumping irrigation solution from the irrigation pump according to predetermined irrigation parameters through the irrigation conduit and the irrigation channel and out the irrigation port in response to receiving the inhalation pressure signal associated with inhalation, wherein the predetermined irrigation parameters include irrigation frequency, irrigation duration, irrigation volume, and irrigation interval of pumping irrigation solution.

14. The synchronized automated bronchial lavage aspiration apparatus of claim 13, wherein the interior channel is a drainage channel and the at least one opening through the catheter is a drainage opening and wherein the drainage opening is formed by a side opening groove along at least a portion of the catheter length in the catheter outer surface.

15. The synchronized automated bronchial lavage aspiration apparatus of claim 14, wherein the catheter further comprises a radio opaque marker.

16. The synchronized automated bronchial lavage aspiration apparatus of claim 14, wherein the catheter has a longitudinal axis along the catheter length and an oval cross section transverse to the longitudinal axis, the oval cross section having opposite vertices, and wherein the at least one drainage opening comprises a pair of drainage openings, wherein each of the pair of drainage openings is aligned with one of the opposite vertices, and wherein each of the pair of drainage openings comprises the drainage channel side opening groove along the catheter outer surface adjacent each opposite vertex.

17. The synchronized automated bronchial lavage aspiration apparatus of claim 14, wherein the catheter has a longitudinal axis along the catheter length and a catheter cross section transverse to the longitudinal axis, and wherein the at least one drainage opening comprises a trio of drainage openings, wherein each of the trio of drainage openings is aligned about the longitudinal axis, and wherein each of the trio of drainage openings comprises the drainage channel side opening groove along the catheter outer surface.

18. The synchronized automated bronchial lavage aspiration apparatus of claim 1, wherein the catheter distal end comprises a split-end catheter having a left catheter end adapted to extend into a left main bronchus and a right catheter end adapted to extend into a right main bronchus.

* * * * *